(12) United States Patent
Achilefu et al.

(10) Patent No.: US 7,504,087 B2
(45) Date of Patent: *Mar. 17, 2009

(54) RECEPTOR-AVID EXOGENOUS OPTICAL CONTRAST AND THERAPEUTIC AGENTS

(75) Inventors: Samuel I. Achilefu, St. Louis, MO (US); Raghavan Rajagopalan, Solon, OH (US); Richard B. Dorshow, St. Louis, MO (US); Joseph E. Bugaj, Richmond, CA (US); Muthunadar P. Periasamy, Chesterfield, MO (US)

(73) Assignee: Mallinkrodt Inc., Hazelwood, MO (US)

( * ) Notice: Subject to any disclaimer, the term of this patent is extended or adjusted under 35 U.S.C. 154(b) by 273 days.

This patent is subject to a terminal disclaimer.

(21) Appl. No.: 11/075,792

(22) Filed: Mar. 9, 2005
(Under 37 CFR 1.47)

(65) Prior Publication Data

US 2005/0281741 A1    Dec. 22, 2005

Related U.S. Application Data

(63) Continuation-in-part of application No. 10/800,531, filed on Mar. 15, 2004, which is a continuation-in-part of application No. 09/864,011, filed on May 23, 2001, now Pat. No. 6,706,254, which is a continuation-in-part of application No. 09/484,322, filed on Jan. 18, 2000, now Pat. No. 6,395,257.

(51) Int. Cl.
*A61K 51/00* (2006.01)
*A61M 36/14* (2006.01)
(52) U.S. Cl. ............... 424/1.69; 424/1.11; 424/1.65
(58) Field of Classification Search ............. 424/1.11, 424/1.65, 1.69, 1.37, 9.1, 9.3, 9.4, 9.5, 9.6, 424/9.7, 9.8; 548/400, 416, 427; 530/300, 530/350, 387; 514/359, 360, 384; 435/1.11; 536/1.11; 534/7; 552/502
See application file for complete search history.

(56) References Cited

U.S. PATENT DOCUMENTS

| | | | | |
|---|---|---|---|---|
| 5,393,654 | A  * | 2/1995 | Burrows et al. | 430/584 |
| 6,190,641 | B1 * | 2/2001 | Achilefu et al. | 424/9.6 |
| 6,238,931 | B1 * | 5/2001 | Buechler et al. | 436/546 |
| 6,264,919 | B1 * | 7/2001 | Achilefu et al. | 424/9.6 |
| 6,395,257 | B1 * | 5/2002 | Achilefu et al. | 424/9.6 |
| 6,630,570 | B1 * | 10/2003 | Licha et al. | 530/324 |
| 6,706,254 | B2 * | 3/2004 | Achilefu et al. | 424/9.6 |
| 6,761,878 | B2 * | 7/2004 | Achilefu et al. | 424/9.6 |
| 7,128,896 | B2 * | 10/2006 | Achilefu et al. | 424/9.6 |

FOREIGN PATENT DOCUMENTS

WO    WO 2005/000218 A2    1/2005

* cited by examiner

*Primary Examiner*—D. L Jones
(74) *Attorney, Agent, or Firm*—Thompson Hine LLP

(57) ABSTRACT

Cyanine and Indocyanine dye compounds and bioconjugates are disclosed. The present invention includes several cyanine and indocyanine dyes, including bioconjugates of the same, with a variety of bis- and tetrakis (carboxylic acid) homologues. The compounds of the invention may be conjugated to bioactive peptides, carbohydrates, hormones, drugs, or other bioactive agents. The small size of compounds of the invention allows favorable delivery to tumor cells as compared to larger molecular weight imaging agents. Further, use of a biocompatible organic solvent such as dimethylsulfoxide may be said to assist in maintaining the fluorescence of compounds of the invention. The compounds and bioconjugates herein disclosed are useful in a variety of medical applications including, but not limited to, diagnostic imaging and therapy, endoscopic applications for the detection of tumors and other abnormalities, localized therapy, photoacoustic tumor imaging, detection and therapy, and sonofluorescence tumor imaging, detection and therapy.

20 Claims, 14 Drawing Sheets

SEQUENCE LISTING

```
<160> NUMBER OF SEQ ID NOS: 8

<210> SEQ ID NO 1
<211> LENGTH: 8
<212> TYPE: PRT
<213> ORGANISM: Artificial Sequence
<220> FEATURE:
<221> NAME/KEY: MOD RES
<222> LOCATION: (1)...(8)
<223> OTHER INFORMATION: Xaa at location 1 represents D-Phe.
      Artificial sequence is completely synthesized.
<220> FEATURE:
<223> OTHER INFORMATION: Xaa at locations 2 and 7 represents Cys with an
      intramolecular disulfide bond between two Cys
      amino acids. Artificial sequence is completely synthesized.
<220> FEATURE:
<223> OTHER INFORMATION: Xaa at location 4 represents D-Trp. Artificial
      sequence is completely synthesized.

<400> SEQUENCE: 1

Xaa Xaa Tyr Xaa Lys Thr Xaa Thr
1               5
```

```
<210> SEQ ID NO 2
<211> LENGTH: 8
<212> TYPE: PRT
<213> ORGANISM: Artificial Sequence
<220> FEATURE:
<221> NAME/KEY: MOD RES
<222> LOCATION: (1)...(8)
<223> OTHER INFORMATION: Xaa at location 1 represents D-Phe. Artificial
      sequence is completely synthesized.
<220> FEATURE:
<223> OTHER INFORMATION: Xaa at locations 2 and 7 represents Cys with an
      intramolecular disulfide bond between two Cys
      amino acids. Artificial sequence is completely synthesized.
<220> FEATURE:
<223> OTHER INFORMATION: Xaa at location 4 represents D-Trp. Artificial
      sequence is completely synthesized.
<220> FEATURE:
<223> OTHER INFORMATION: Xaa at location 8 represents Thr-OH. Artificial
      sequence is completely synthesized.

<400> SEQUENCE: 2

Xaa Xaa Tyr Xaa Lys Thr Xaa Xaa
 1               5

<210> SEQ ID NO 3
<211> LENGTH: 11
<212> TYPE: PRT
<213> ORGANISM: Unknown
<220> FEATURE:
<221> NAME/KEY: MOD RES
<222> LOCATION: (1)...(11)
<223> OTHER INFORMATION: Bombesin analog

<400> SEQUENCE: 3

Gly Ser Gly Gln Trp Ala Val Gly His Leu Met
 1               5                  10

<210> SEQ ID NO 4
<211> LENGTH: 11
<212> TYPE: PRT
<213> ORGANISM: Unknown
<220> FEATURE:
<221> NAME/KEY: MOD_RES
<222> LOCATION: (1)...(11)
<223> OTHER INFORMATION: Bombesin analog

<400> SEQUENCE: 4

Gly Asp Gly Gln Trp Ala Val Gly His Leu Met
 1               5                  10

<210> SEQ ID NO 5
<211> LENGTH: 8
<212> TYPE: PRT
<213> ORGANISM: Unknown
<220> FEATURE:
<221> NAME/KEY: MOD_RES
<222> LOCATION: (1)...(8)
<223> OTHER INFORMATION: Cholecystokinin octapeptide analogs

<400> SEQUENCE: 5

Asp Tyr Met Gly Trp Met Asp Phe
 1               5

<210> SEQ ID NO 6
<211> LENGTH: 8
<212> TYPE: PRT
<213> ORGANISM: Artificial Sequence
<220> FEATURE:
<221> NAME/KEY: MOD RES
<222> LOCATION: (1)...(6)
<223> OTHER INFORMATION: Xaa at locations 3 and 6 represents Norleucine.
```

```
                               -continued

Artificial sequence is completely synthesized.

<400> SEQUENCE: 6

Asp Tyr Xaa Gly Trp Xaa Asp Phe
 1               5

<210> SEQ ID NO 7
<211> LENGTH: 8
<212> TYPE: PRT
<213> ORGANISM: Artificial Sequence
<220> FEATURE:
<221> NAME/KEY: MOD RES
<222> LOCATION: (1)...(8)
<223> OTHER INFORMATION: Xaa at location 1 represents D-Asp. Artificial
      sequence is completely synthesized.
<220> FEATURE:
<223> OTHER INFORMATION: Xaa at locations 3 and 6 represents Norleucine.
      Artificial sequence is completely synthesized.

<400> SEQUENCE: 7

Xaa Tyr Xaa Gly Trp Xaa Asp Phe
 1               5

<210> SEQ ID NO 8
<211> LENGTH: 8
<212> TYPE: PRT
<213> ORGANISM: Artificial Sequence
<220> FEATURE:
<221> NAME/KEY: MOD RES
<222> LOCATION: (1)...(8)
<223> OTHER INFORMATION: Xaa at location 1 represents D-Lys. Artificial
      sequence is completely synthesized.

<400> SEQUENCE: 8

Xaa Pro Arg Arg Pro Tyr Ile Leu
 1               5
```

RECEPTOR-AVID EXOGENOUS OPTICAL CONTRAST AND THERAPEUTIC AGENTS

REFERENCE TO RELATED APPLICATIONS

This application is a continuation-in-part of co-pending U.S. patent application Ser. No. 10/800,531 filed Mar. 15, 2004, which is a continuation-in-part of Ser. No. 09/864,011, now U.S. Pat. No. 6,706,254 filed May 23, 2001, which is a continuation-in-part of Ser. No. 09/484,322, now U.S. Pat. No. 6,395,257 filed Jan. 18, 2000, each of which is expressly incorporated by reference herein it is entirety.

FIELD OF INVENTION

This invention relates generally to compositions of cyanine and indocyanine dye bioconjugates with bioactive molecules for diagnosis and therapy, and particularly for visualization and detection of tumors.

BACKGROUND OF THE INVENTION

Several dyes that absorb and emit light in the visible and near-infrared region of electromagnetic spectrum are currently being used for various biomedical applications due to their biocompatibility, high molar absorptivity, and/or high fluorescence quantum yields. The high sensitivity of the optical modality in conjunction with dyes as contrast agents parallels that of nuclear medicine, and permits visualization of organs and tissues without the undesirable effect of ionizing radiation.

Cyanine dyes with intense absorption and emission in the near-infrared (NIR) region are particularly useful because biological tissues are optically transparent in this region (B. C. Wilson, Optical properties of tissues. *Encyclopedia of Human Biology,* 1991, 5, 587-597). For example, indocyanine green, which absorbs and emits in the NIR region, has been used for monitoring cardiac output, hepatic functions, and liver blood flow (Y-L. He, et al., Measurement of blood volume using indocyanine green measured with pulse-spectrometry: Its reproducibility and reliability. *Critical Care Medicine,* 1998, 26(8), 1446-1451; J. Caesar, et al., The use of Indocyanine green in the measurement of hepatic blood flow and as a test of hepatic function. *Clin. Sci.* 1961, 21, 43-57), and its functionalized derivatives have been used to conjugate biomolecules for diagnostic purposes (R. B. Mujumdar, et al., Cyanine dye labeling reagents: Sulfoindocyanine succinimidyl esters. *Bioconjugate Chemistry,* 1993, 4(2), 105-111; U.S. Pat. No. 5,453,505; WO 98/48846; WO 98/22146; WO 96/17628; WO 98/48838).

A major drawback in the use of cyanine dye derivatives is the potential for hepatobiliary toxicity resulting from the rapid clearance of these dyes by the liver (G. R. Cherrick, et al., Indocyanine green: Observations on its physical properties, plasma decay, and hepatic extraction. *J. Clinical Investigation,* 1960, 39, 592-600). This is associated with the tendency of cyanine dyes in solution to form aggregates, which could be taken up by Kupffer cells in the liver.

Various attempts to obviate this problem have not been very successful. Typically, hydrophilic peptides, polyethyleneglycol or oligosaccharide conjugates have been used, but these resulted in long-circulating products, which are eventually still cleared by the liver. Another major difficulty with current cyanine and indocyanine dye systems is that they offer a limited scope in the ability to induce large changes in the absorption and emission properties of these dyes. Attempts have been made to incorporate various heteroatoms and cyclic moieties into the polyene chain of these dyes (L. Strekowski, et al., Substitution reactions of a nucleofugal group in hetamethine cyanine dyes. *J. Org. Chem.,* 1992, 57, 4578-4580; N. Narayanan, and G. Patonay, A new method for the synthesis of heptamethine cyanine dyes: Synthesis of new near infrared fluorescent labels. *J. Org. Chem.,* 1995, 60, 2391-2395; U.S. Pat. Nos. 5,732,104; 5,672,333; and 5,709, 845), but the resulting dye systems do not show large differences in absorption and emission maxima, especially beyond 830 nm where photoacoustic diagnostic applications are very sensitive. They also possess a prominent hydrophobic core, which enhances liver uptake. Further, most cyanine dyes do not have the capacity to form starburst dendrimers, which are useful in biomedical applications.

For the purpose of tumor detection, many conventional dyes are useful for in vitro applications because of their highly toxic effect on both normal and abnormal tissues. Other dyes lack specificity for particular organs or tissues and, hence, these dyes must be attached to bioactive carriers such as proteins, peptides, carbohydrates, and the like to deliver the dyes to specific regions in the body. Several studies on the use of near infrared dyes and dye-biomolecule conjugates have been published (G. Patonay and M. D. Antoine, Near-Infrared Fluorogenic Labels: New Approach to an Old Problem, *Analytical Chemistry,* 1991, 63:321A-327A and references therein; M. Brinkley, A Brief Survey of Methods for Preparing Protein Conjugates with Dyes, Haptens, and Cross-Linking Reagents, *Perspectives in Bioconjugate Chemistry* 1993, pp. 59-70, C. Meares (Ed), ACS Publication, Washington, D.C.; J. Slavik, *Fluorescent Probes in Cellular and Molecular Biology,* 1994, CRC Press, Inc.; U.S. Pat. No. 5,453,505; WO 98/48846; WO 98/22146; WO 96/17628; WO 98/48838). Of particular interest is the targeting of tumor cells with antibodies or other large protein carriers such as transferrin as delivery vehicles (A. Becker, et al., "Transferrin Mediated Tumor Delivery of Contrast Media for Optical Imaging and Magnetic Resonance Imaging", Biomedical Optics meeting, Jan. 23-29, 1999, San Jose, Calif.). Such an approach has been widely used in nuclear medicine applications. Its major advantage is the retention of a carrier's tissue specificity, since the molecular volume of the dye is substantially smaller than the carrier. However, this approach does have some serious limitations in that the diffusion of high molecular weight bioconjugates to tumor cells is highly unfavorable, and is further complicated by the net positive pressure in solid tumors (R. K. Jain, Barriers to Drug Delivery in Solid Tumors, *Scientific American* 1994, 271:58-65. Furthermore, many dyes in general, and cyanine dyes, in particular, tend to form aggregates in aqueous media that lead to fluorescence quenching.

Therefore, there is a need for dyes that could prevent dye aggregation in solution, that are predisposed to form dendrimers, that are capable of absorbing or emitting beyond 800 nm, that possess desirable photophysical properties, and that are endowed with tissue-specific targeting capability.

SUMMARY OF THE INVENTION

The invention is directed to compositions, as well as methods of preparing such compositions, of low molecular weight biomolecule-dye conjugates. These bioconjugates may be utilized, for example, to enhance tumor detection. Compositions of the present invention preserve the fluorescence efficiency of the dye molecules, do not aggregate in solution, form starburst dendrimers, are capable of absorbing and/or omitting light in the near infrared region (beyond 800 mm), and can be rendered tissue-specific.

In one aspect, the present invention relates to a composition including a cyanine dye of general formula 1

Formula 1

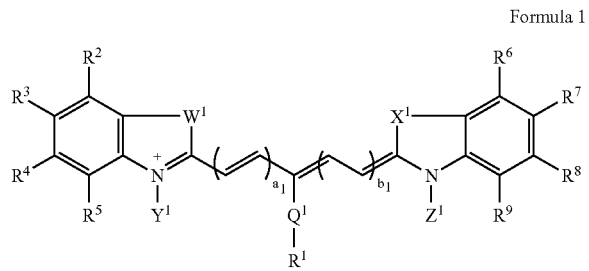

wherein $W^1$ and $X^1$ may be the same or different and are selected from the group consisting of —$CR^wR^x$, —O—, —$NR^y$, —S—, and —Se—; $Q^2$ is a single bond or is selected from the group consisting of —O—, —S—, —Se—; and —$NR^5$; $a_1$ and $b_1$ independently vary from 0 to 5; a and c are independently from 1 to 20; b and d are independently from 1 to 100; $Y^1$ is a constituent selected from the group consisting of hydrogen, $C_1$-$C_{10}$ alkyl, $C_5$-$C_{20}$ aryl, $C_1$-$C_{10}$ alkoxyl, $C_1$-$C_{10}$ polyalkoxyalkyl, $C_1$-$C_{20}$ polyhydroxyalkyl, $C_5$-$C_{20}$ polyhydroxyaryl, $C_1$-$C_{10}$ aminoalkyl, —$CH_2(CH_2OCH_2)_b$—$CH_2$—OH, —$(CH_2)_a$—$CO_2H$, —$(CH_2)_a$—CONH-Bm, —$CH_2$—$(CH_2OCH_2)_b$—$CH_2$—CONH-Bm, —$(CH_2)_a$—NHCO-Bm, —$CH_2$—$(CH_2OCH_2)_b$—$CH_2$—NHCO-Bm, —$(CH_2)_{a-N(R^y)}$—$(CH_2)_b$—CONH-Bm, $(CH_2)_a$—$N(R^y)$—$(CH_2)_c$—NHCO-Bm, —$(CH_2)_a$—$N(R^y)$—$CH_2$—$(CH_2OCH_2)_b$—$CH_2$—CONH-Bm, —$(CH_2)_a$—$N(R^y)$—$CH_2$—$(CH_2OCH_2)_b$—$CH_2$—NHCO-Bm, —$CH_2$—$(CH_2OCH_2)_b$—$CH_2$—$N(R^y)$—$(CH_2)_a$—CONH-Bm, —$CH_2$—$(CH_2OCH_2)_b$—$CH_2$—$N(R^y)$—$(CH_2)_a$—NHCO-Bm, —$CH_2$—$(CH_2OCH_2)_b$—$CH_2$—$N(R^y)$—$CH_2$—$(CH_2OCH_2)_d$—CONH-Bm, —$CH_2$—$(CH_2OCH_2)_b$—$CH_2$—$N(R^y)$—$CH_2$—$(CH_2OCH_2)_d$—NHCO-Bm, —$(CH_2)_a$—$NR^yR^z$, and —$CH_2(CH_2OCH_2)_b$—$CH_2NR^yR^z$; $Z^1$ is a constituent selected from the group consisting of hydrogen, $C_1$-$C_{10}$ alkyl, $C_5$-$C_{20}$ aryl, $C_1$-$C_{10}$ alkoxyl, $C_1$-$C_{10}$ polyalkoxyalkyl, $C_1$-$C_{20}$ polyhydroxyalkyl, $C_5$-$C_{20}$ polyhydroxyaryl, $C_1$-$C_{10}$ aminoalkyl, —$CH_2(CH_2OCH_2)_b$—$CH_2$—OH, —$(CH_2)_a$—$CO_2H$, —$(CH_2)_a$—CONH-Dm, —$CH_2$—$(CH_2OCH_2)_b$—$CH_2$—CONH-Dm, —$(CH_2)_a$—NHCO-Dm, —$CH_2$—$(CH_2OCH_2)_b$—$CH_2$—NHCO-Dm, —$(CH_2)_a$—$N(R^y)$—$(CH_2)_b$—CONH-Dm, $(CH_2)_a$—$N(R^y)$—$(CH_2)_c$—NHCO-Dm, —$(CH_2)_a$—$N(R^y)$—$CH_2$—$(CH_2OCH_2)_b$—$CH_2$—CONH-Dm, —$(CH_2)_a$—$N(R^y)$—$CH_2$—$(CH_2OCH_2)_b$—$CH_2$—NHCO-Dm, —$CH_2$—$(CH_2OCH_2)_b$—$CH_2$—$N(R^y)$—$(CH_2)_a$—CONH-Dm, —$CH_2$—$(CH_2OCH_2)_b$—$CH_2$—$N(R^y)$—$(CH_2)_a$—NHCO-Dm, —$CH_2$—$(CH_2OCH_2)_b$—$CH_2$—$N(R^y)$—$CH_2$—$(CH_2OCH_2)_d$—CONH-Dm, —$CH_2$—$(CH_2OCH_2)_b$—$CH_2$—$N(R^y)$—$CH_2$—$(CH_2OCH_2)_d$—NHCO-Dm, —$(CH_2)_a$—$NR^yR^z$, and —$CH_2(CH_2OCH_2)_b$—$CH_2NR^yR^z$; $R^w$, $R^x$, $R^y$, $R^z$, and $R^1$ to $R^9$ are independently selected from the group consisting of hydrogen, $C_1$-$C_{10}$ alkyl, $C_5$-$C_{20}$ aryl, $C_1$-$C_{10}$ alkoxyl, $C_1$-$C_{10}$ polyalkoxyalkyl, $C_1$-$C_{20}$ polyhydroxyalkyl, $C_5$-$C_{20}$ polyhydroxyaryl, $C_1$-$C_{10}$ aminoalkyl, glucose derivatives of R groups, cyano, nitro, halogen, saccharide, peptide, —$CH_2(CH_2OCH_2)_b$—$CH_2$—OH, —$(CH_2)_a$—$CO_2H$, —$(CH_2)_a$—CONH-Bm, —$CH_2$—$(CH_2OCH_2)_b$—$CH_2$—CONH-Bm, —$(CH_2)_a$—NHCO-Bm, —$CH_2$—$(CH_2OCH_2)_b$—$CH_2$—NHCO-Bm; —$(CH_2)_a$—OH and —$CH_2$—$(CH_2OCH_2)_b$—$CO_2H$; and Bm and Dm are independently selected from the group consisting of a peptide, a protein, a cell, an antibody, an antibody fragment, a saccharide, a glycopeptide, a peptidomimetic, a drug, a drug mimic, a hormone, a metal chelating agent, a radioactive or nonradioactive metal complex, a photosensitizer for phototherapy, and an echogenic agent. At least one of $Y^1$, $Z^1$, $R^w$, $R^x$, $R^y$, $R^z$, $R^1$, $R^2$, $R^3$, $R^4$, $R^5$, $R^6$, $R^7$, $R^8$ and $R^9$ is preferably a constituent including Bm or Dm. Further, it is preferred that at least one Bm or Dm of the cyanine dye is selected from the group consisting of a peptide, a protein, a cell, a metal chelating agent, a radioactive or nonradioactive metal complex, a photosensitizer for phototherapy, and an echogenic agent. For instance, in one preferred family of embodiments, at least one of $Y^1$, $Z^1$, $R^w$, $R^x$, $R^y$, $R^z$, $R^1$, $R^2$, $R^3$, $R^4$, $R^5$, $R^6$, $R^7$, $R^8$ and $R^9$ is a constituent including Bm or Dm, and at least one of Bm and Dm is a peptide such as Octreotide, Octreotate, Bombesin, Cholecystokinin, or Neurotensin. In another exemplary family of preferred embodiments, at least one of $Y^1$, $Z^1$, $R^w$, $R^x$, $R^y$, $R^z$, $R^1$, $R^2$, $R^3$, $R^4$, $R^5$, $R^6$, $R^7$, $R^8$ and $R^9$ is a constituent including Bm or Dm, and at least one of Bm and Dm is a photosensitizer for phototherapy.

In another aspect, the present invention relates to a composition including an indocyanine dye of general formula 2

Formula 2

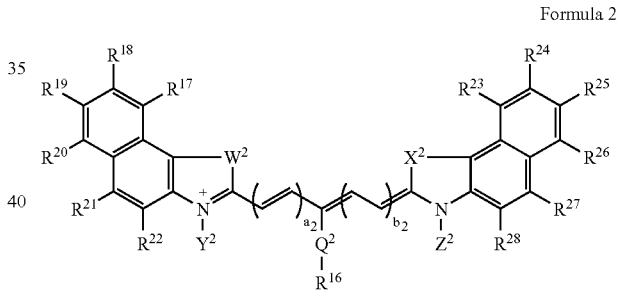

wherein $W^2$ and $X^2$ may be the same or different and are selected from the group consisting of —$CR^1R^2$, —O—, —$NR^3$, —S—, and —Se—; $Q^2$ is a single bond or is selected from the group consisting of —O—, —S—, —Se—; and —$NR^5$; $a_2$ and $b_2$ independently vary from 0 to 5; a and c are independently from 1 to 20; b and d are independently from 1 to 100; $Y^2$ is selected from the group consisting of hydrogen, $C_1$-$C_{10}$ alkyl, $C_5$-$C_{20}$ aryl, $C_1$-$C_{10}$ alkoxyl, $C_1$-$C_{10}$ polyalkoxyalkyl, $C_1$-$C_{20}$ polyhydroxyalkyl, $C_5$-$C_{20}$ polyhydroxyaryl, $C_1$-$C_{10}$ aminoalkyl, —$CH_2(CH_2OCH_2)_b$—$CH_2$—OH, —$(CH_2)_a$—$CO_2H$, —$(CH_2)_a$—CONH-Bm, —$CH_2$—$(CH_2OCH_2)_b$—$CH_2$—CONH-Bm, —$(CH_2)_a$—NHCO-Bm, —$CH_2$—$(CH_2OCH_2)_b$—$CH_2$—NHCO-Bm, —$(CH_2)_a$—$N(R^3)$—$(CH_2)_b$—CONH-Bm, $(CH_2)_a$—$N(R^3)$—$(CH_2)_c$—NHCO-Bm, —$(CH_2)_a$—$N(R^3)$—$CH_2$—$(CH_2OCH_2)_b$—$CH_2$—CONH-Bm, —$(CH_2)_a$—$N(R^3)$—$CH_2$—$(CH_2OCH_2)_b$—$CH_2$—NHCO-Bm, —$CH_2$—$(CH_2OCH_2)_b$—$CH_2$—$N(R^3)$—$(CH_2)_a$—CONH-Bm, —$CH_2$—$(CH_2OCH_2)_b$—$CH_2$—$N(R^3)$—$(CH_2)_a$—NHCO-Bm, —$CH_2$—$(CH_2OCH_2)_b$—$CH_2$—$N(R^3)$—$CH_2$—

$-(CH_2OCH_2)_d-CONH-Bm$, $-CH_2-(CH_2OCH_2)_b-CH_2-N(R^3)-CH_2-(CH_2OCH_2)_d-NHCO-Bm$, $-(CH_2)_a-NR^3R^4$, and $-CH_2(CH_2OCH_2)_b-CH_2NR^3R^4$; $Z^2$ is selected from the group consisting of hydrogen, $C_1-C_{10}$ alkyl, $C_5-C_{20}$ aryl, $C_1-C_{10}$ alkoxyl, $C_1-C_{10}$ polyalkoxyalkyl, $C_1-C_{20}$ polyhydroxyalkyl, $C_5-C_{20}$ polyhydroxyaryl, $C_1-C_{10}$ aminoalkyl, $-CH_2(CH_2OCH_2)_b-CH_2-OH$, $-(CH_2)_a-CO_2H$, $-(CH_2)_a-CONH-Dm$, $-CH_2-(CH_2OCH_2)_b-CH_2-CONH-Dm$, $-(CH_2)_a-NHCO-Dm$, $-CH_2-(CH_2OCH_2)_b-CH_2-NHCO-Dm$, $-(CH_2)_a-N(R^3)-(CH_2)_b-CONH-Dm$, $(CH_2)_a-N(R^3)-(CH_2)_c-NHCO-Dm$, $-(CH_2)_a-N(R^3)-CH_2-(CH_2OCH_2)_b-CH_2-CONH-Dm$, $-(CH_2)_a-N(R^3)-CH_2-(CH_2OCH_2)_b-CH_2-NHCO-Dm$, $-CH_2-(CH_2OCH_2)_b-CH_2-N(R^3)-(CH_2)_a-CONH-Dm$, $-CH_2-(CH_2OCH_2)_b-CH_2-N(R^3-(CH_2)_a-NHCO-Dm$, $-CH_2-(CH_2OCH_2)_b-CH_2-N(R^3)-CH_2-(CH_2OCH_2)_d-CONH-Dm$, $-CH_2-(CH_2OCH_2)_b-CH_2-N(R^3)-CH_2-(CH_2OCH_2)_d-NHCO-Dm$, $-(CH_2)_a-NR^3R^4$, and $-CH_2(CH_2OCH_2)_b-CH_2NR^3R^4$; $R^1$ to $R^5$, and $R^{16}$ to $R^{28}$ are constituents independently selected from the group consisting of hydrogen, $C_1-C_{10}$ alkyl, $C_5-C_{20}$ aryl, $C_1-C_{10}$ alkoxyl, $C_1-C_{10}$ polyalkoxyalkyl, $C_1-C_{20}$ polyhydroxyalkyl, $C_5-C_{20}$ polyhydroxyaryl, $C_1-C_{10}$ aminoalkyl, glucose derivatives of R groups, cyano, nitro, halogen, saccharide, peptide, $-CH_2(CH_2OCH_2)_b-CH_2-OH$, $-(CH_2)_a-CO_2H$, $-(CH_2)_a-CONH-Bm$, $-CH_2-(CH_2OCH_2)_b-CH_2-CONH-Bm$, $-(CH_2)_a-NHCO-Bm$, $-CH_2-(CH_2OCH_2)_b-CH_2-NHCO-Bm$, $-(CH_2)_a-OH$ and $-CH_2-(CH_2OCH_2)_b-CO_2H$; and Bm and Dm are independently selected from the group consisting of a peptide, a protein, a cell, an antibody, an antibody fragment, a saccharide, a glycopeptide, a peptidomimetic, a drug, a drug mimic, a hormone, a metal chelating agent, a radioactive or nonradioactive metal complex, a photosensitizer for phototherapy, and an echogenic agent. At least one of $Y^2$, $Z^2$, $R^1$, $R^2$, $R^3$, $R^4$, $R^5$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$ and $R^{28}$ is preferably a constituent including Bm or Dm. Further, it is preferred that at least one Bm or Dm of the indocyanine dye is selected from the group consisting of a peptide, a protein, a cell, a metal chelating agent, a radioactive or nonradioactive metal complex, a photosensitizer for phototherapy, and an echogenic agent. For instance, in one preferred family of embodiments, at least one of $Y^2$, $Z^2$, $R^1$, $R^2$, $R^3$, $R^4$, $R^5$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$ and $R^{28}$ is a constituent including Bm or Dm, and at least one of Bm and Dm is a peptide such as Octreotide, Octreotate, Bombesin, Cholecystokinin, or Neurotensin. In another exemplary family of preferred embodiments, at least one of $Y^1$, $Z^1$, $R^w$, $R^x$, $R^y$, $R^z$, $R^1$, $R^2$, $R^3$, $R^4$, $R^5$, $R^6$, $R^7$, $R^8$ and $R^9$ is a constituent including Bm or Dm, and at least one of Bm and Dm is a photosensitizer for phototherapy.

In yet another aspect, the invention relates to a composition including a cyanine dye of general formula 3

Formula 3

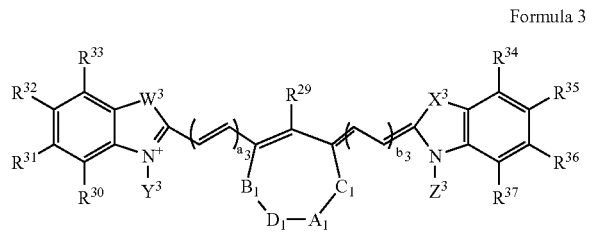

wherein $W^3$ and $X^3$ may be the same or different and are selected from the group consisting of $-CR^1R^2$, $-O-$, $-NR^3$, $-S-$, and $-Se$; $Y^3$ is selected from the group consisting of hydrogen, $C_1-C_{10}$ alkyl, $C_5-C_{20}$ aryl, $C_1-C_{10}$ alkoxyl, $C_1-C_{10}$ polyalkoxyalkyl, $C_1-C_{20}$ polyhydroxyalkyl, $C_5-C_{20}$ polyhydroxyaryl, $C_1-C_{10}$ aminoalkyl, $-CH_2(CH_2OCH_2)_b-CH_2-OH$, $-(CH_2)_a-CO_2H$, $-(CH_2)_a-CONH-Bm$, $-CH_2-(CH_2OCH_2)_b-CH_2-CONH-Bm$, $-(CH_2)_a-NHCO-Bm$, $-CH_2-(CH_2OCH_2)_b-CH_2-NHCO-Bm$, $-(CH_2)_a-N(R^3)-(CH_2)_b-CONH-Bm$, $-(CH_2)_a-N(R^3)-(CH_2)_c-NHCO-Bm$, $-(CH_2)_a-N(R^3)-CH_2-(CH_2OCH_2)_b-CH_2-CONH-Bm$, $-(CH_2)_a-N(R^3)-CH_2-(CH_2OCH_2)_b-CH_2-NHCO-Bm$, $-CH_2-(CH_2OCH_2)_b-CH_2-N(R^3)-(CH_2)_a-CONH-Bm$, $-CH_2-(CH_2OCH_2)_b-CH_2-N(R^3)-(CH_2)_a-NHCO-Bm$, $-CH_2-(CH_2OCH_2)_b-CH_2-N(R^3)-CH_2-(CH_2OCH_2)_d-CONH-Bm$, $-CH_2-(CH_2OCH_2)_b-CH_2-N(R^3)-CH_2-(CH_2OCH_2)_d-NHCO-Bm$, $-(CH_2)_a-NR^3R^4$, and $-CH_2(CH_2OCH_2)_b-CH_2NR^3R^4$; $Z^3$ is selected from the group consisting of hydrogen, $C_1-C_{10}$ alkyl, $C_5-C_{20}$ aryl, $C_1-C_{10}$ alkoxyl, $C_1-C_{10}$ polyalkoxyalkyl, $C_1-C_{20}$ polyhydroxyalkyl, $C_5-C_{20}$ polyhydroxyaryl, $C_1-C_{10}$ aminoalkyl, $-CH_2(CH_2OCH_2)_b-CH_2-OH$, $-(CH_2)_a-CO_2H$, $-(CH_2)_a-CONH-Dm$, $-CH_2-(CH_2OCH_2)_b-CH_2-CONH-Dm$, $-(CH_2)_a-NHCO-Dm$, $-CH_2-(CH_2OCH_2)_b-CH_2-NHCO-Dm$, $-(CH_2)_a-N(R^3)-(CH_2)_b-CONH-Dm$, $(CH_2)_a-N(R^3)-(CH_2)_c-NHCO-Dm$, $-(CH_2)_a-N(R^3)-CH_2-(CH_2OCH_2)_b-CH_2-CONH-Dm$, $-(CH_2)_a-N(R^3)-CH_2-(CH_2OCH_2)_b-CH_2-NHCO-Dm$, $-CH_2-(CH_2OCH_2)_b-CH_2-N(R^3)-(CH_2)_a-CONH-Dm$, $-CH_2-(CH_2OCH_2)_b-CH_2-N(R^3)-(CH_2)_a-NHCO-Dm$, $-CH_2-(CH_2OCH_2)_b-CH_2-N(R^3)-CH_2-(CH_2OCH_2)_d-CONH-Dm$, $-CH_2-(CH_2OCH_2)_b-CH_2-N(R^3)-CH_2-(CH_2OCH_2)_d-NHCO-Dm$, $-(CH_2)_a-NR^3R^4$, and $-CH_2(CH_2OCH_2)_b-CH_2NR^3R^4$; $A_1$ is a single or a double bond; $B_1$, $C_1$, and $D_1$ may the same or different and are selected from the group consisting of $-O-$, $-S-$, $-Se-$, $-P-$, $-CR^1R^2$, $-CR^1$, alkyl, $NR^3$, and $-C=O$; $A_1$, $B_1$, $C_1$, and $D_1$ may together form a 6- to 12-membered carbocyclic ring or a 6- to 12-membered heterocyclic ring optionally containing one or more oxygen, nitrogen, or sulfur atom; $a_3$ and $b_3$ independently vary from 0 to 5; $R^1$ to $R^4$, and $R^{29}$ to $R^{37}$ are independently selected from the group consisting of hydrogen, $C_1-C_{10}$ alkyl, $C_5-C_{20}$ aryl, $C_1-C_{10}$ alkoxyl, $C_1-C_{10}$ polyalkoxyalkyl, $C_1-C_{20}$ polyhydroxyalkyl, $C_5-C_{20}$ polyhydroxyaryl, $C_1-C_{10}$ aminoalkyl, glucose derivatives of R groups, cyano, nitro, halogen, saccharide, peptide, $-CH_2(CH_2OCH_2)_b-CH_2-OH$, $-(CH_2)_a-CO_2H$, $-(CH_2)_a-CONH-Bm$, $-CH_2-(CH_2OCH_2)_b-CH_2-CONH-Bm$, $-(CH_2)_a-NHCO-Bm$, $-CH_2-(CH_2OCH_2)_b-CH_2-NHCO-Bm$, $-(CH_2)_a-OH$ and $-CH_2-(CH_2OCH_2)_b-CO_2H$; Bm and Dm are independently selected from the group consisting of a peptide, a protein, a cell, an antibody, an antibody fragment, a saccharide, a glycopeptide, a peptidomimetic, a drug, a drug mimic, a hormone, a metal chelating agent, a radioactive or nonradioactive metal complex, a photosensitizer for phototherapy, and an echogenic agent; a and c are independently from 1 to 20; and b and d are independently from 1 to 100.

In still another aspect, the invention is directed to a composition including an indocyanine dye of general formula 4

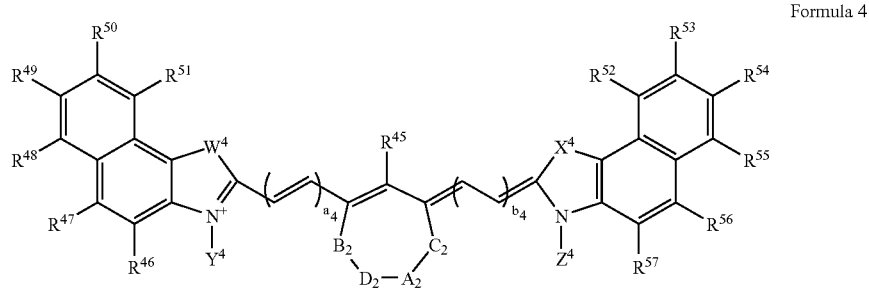

Formula 4 wherein $W^4$ and $X^4$ may be the same or different and are selected from the group consisting of —$CR^1R^2$, —O—, —$NR^3$, —S—, and —Se; $Y^4$ is selected from the group consisting of hydrogen, $C_1$-$C_{10}$ alkyl, $C_5$-$C_{20}$ aryl, $C_1$-$C_{10}$ alkoxyl, $C_1$-$C_{10}$ polyalkoxyalkyl, $C_1$-$C_{20}$ polyhydroxyalkyl, $C_5$-$C_{20}$ polyhydroxyaryl, $C_1$-$C_{10}$ aminoalkyl, —$CH_2$($CH_2OCH_2$)$_b$—$CH_2$—OH, —($CH_2$)$_a$—$CO_2$H, —($CH_2$)$_a$—CONH-Bm, —$CH_2$—($CH_2OCH_2$)$_b$—$CH_2$—CONH-Bm, —($CH_2$)$_a$—NHCO-Bm, —$CH_2$—($CH_2OCH_2$)$_b$—$CH_2$—NHCO-Bm, —($CH_2$)$_a$—N($R^3$)—($CH_2$)$_b$—CONH-Bm, ($CH_2$)$_a$—N($R^3$)—($CH_2$)$_c$—NHCO-Bm, —($CH_2$)$_a$—N($R^3$)—$CH_2$—($CH_2OCH_2$)$_b$—$CH_2$—CONH-Bm, —($CH_2$)$_a$—N($R^3$)—$CH_2$—($CH_2OCH_2$)$_b$—$CH_2$—NHCO-Bm, —$CH_2$—($CH_2OCH_2$)$_b$—$CH_2$—N($R^3$)—($CH_2$)$_a$—CONH-Bm, —$CH_2$—($CH_2OCH_2$)$_b$—$CH_2$—N($R^3$)—($CH_2$)$_a$—NHCO-Bm, —$CH_2$—($CH_2OCH_2$)$_b$—$CH_2$—N($R^3$)—$CH_2$—($CH_2OCH_2$)$_d$—CONH-Bm, —$CH_2$—($CH_2OCH_2$)$_b$—$CH_2$—N($R^3$)—$CH_2$—($CH_2OCH_2$)$_d$—NHCO-Bm, —($CH_2$)$_a$—$NR^3R^4$, and —$CH_2$($CH_2OCH_2$)$_b$—$CH_2NR^3R^4$; $Z^4$ is selected from the group consisting of hydrogen, $C_1$-$C_{10}$ alkyl, $C_5$-$C_{20}$ aryl, $C_1$-$C_{10}$ alkoxyl, $C_1$-$C_{10}$ polyalkoxyalkyl, $C_1$-$C_{20}$ polyhydroxyalkyl, $C_5$-$C_{20}$ polyhydroxyaryl, $C_1$-$C_{10}$ aminoalkyl, —$CH_2$($CH_2OCH_2$)$_b$—$CH_2$—OH, —($CH_2$)$_a$—$CO_2$H, —($CH_2$)$_a$—CONH-Dm, —$CH_2$—($CH_2OCH_2$)$_b$—$CH_2$—CONH-Dm, —($CH_2$)$_a$—NHCO-Dm, —$CH_2$—($CH_2OCH_2$)$_b$—$CH_2$—NHCO-Dm, —($CH_2$)$_a$—N($R^3$)—($CH_2$)$_b$—CONH-Dm, ($CH_2$)$_a$—N($R^3$)—($CH_2$)$_c$—NHCO-Dm, —($CH_2$)$_a$—N($R^3$)—$CH_2$—($CH_2OCH_2$)$_b$—$CH_2$—CONH-Dm, —($CH_2$)$_a$—N($R^3$)—$CH_2$—($CH_2OCH_2$)$_b$—$CH_2$—NHCO-Dm, —$CH_2$—($CH_2OCH_2$)$_b$—$CH_2$—N($R^3$)—($CH_2$)$_a$—CONH-Dm, —$CH_2$—($CH_2OCH_2$)$_b$—$CH_2$—N($R^3$)—($CH_2$)$_a$—NHCO-Dm, —$CH_2$—($CH_2OCH_2$)$_b$—$CH_2$—N($R^3$)—$CH_2$—($CH_2OCH_2$)$_d$—CONH-Dm, —$CH_2$—($CH_2OCH_2$)$_b$—$CH_2$—N($R^3$)—$CH_2$—($CH_2OCH_2$)$_d$—NHCO-Dm, —($CH_2$)$_a$—$NR^3R^4$, and —$CH_2$($CH_2OCH_2$)$_b$—$CH_2NR^3R^4$; $A_2$ is a single or a double bond; $B_2$, $C_2$, and $D_2$ may be the same or different and are selected from the group consisting of —O—, —S—, —Se—, —P—, —$CR^1R^2$, —$CR^1$, alkyl, $NR^3$, and —C=O; $A_2$, $B_2$, $C_2$, and $D_2$ may together form a 6- to 12-membered carbocyclic ring or a 6- to 12-membered heterocyclic ring optionally containing one or more oxygen, nitrogen, or sulfur atom; $a_4$ and $b_4$ independently vary from 0 to 5; $R^1$ to $R^4$, and $R^{45}$ to $R^{57}$ are independently selected from the group consisting of hydrogen, $C_1$-$C_{10}$ alkyl, $C_5$-$C_{20}$ aryl, $C_1$-$C_{10}$ alkoxyl, $C_1$-$C_{10}$ polyalkoxyalkyl, $C_1$-$C_{20}$ polyhydroxyalkyl, $C_5$-$C_{20}$ polyhydroxyaryl, $C_1$-$C_{10}$ aminoalkyl, glucose derivatives of R groups, cyano, nitro, halogen, saccharide, peptide, —$CH_2$($CH_2OCH_2$)$_b$—$CH_2$—OH, —($CH_2$)$_a$—$CO_2$H, —($CH_2$)$_a$—CONH-Bm, —$CH_2$—($CH_2OCH_2$)$_b$—$CH_2$—CONH-Bm, —($CH_2$)$_a$—NHCO-Bm, —$CH_2$—($CH_2OCH_2$)$_b$—$CH_2$—NHCO-Bm, —($CH_2$)$_a$—OH and —$CH_2$—($CH_2OCH_2$)$_b$—$CO_2$H; Bm and Dm are independently selected from the group consisting of a peptide, a protein, a cell, an antibody, an antibody fragment, a saccharide, a glycopeptide, a peptidomimetic, a drug, a drug mimic, a hormone, a metal chelating agent, a radioactive or nonradioactive metal complex, a photosensitizer for phototherapy, and an echogenic agent; a and c are independently from 1 to 20; and b and d are independently from 1 to 100.

Yet another aspect of the present invention relates to a composition including a cyanine dye of general formula 5

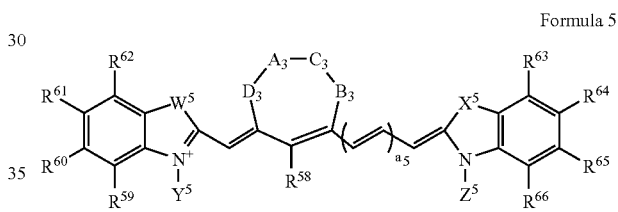

Formula 5 wherein $W^5$ and $X^5$ may be the same or different and are selected from the group consisting of —$CR^1R^2$, —O—, —$NR^3$, —S—, and —Se; $Y^5$ is selected from the group consisting of hydrogen, $C_1$-$C_{10}$ alkyl, $C_5$-$C_{20}$ aryl, $C_1$-$C_{10}$ alkoxyl, $C_1$-$C_{10}$ polyalkoxyalkyl, $C_1$-$C_{20}$ polyhydroxyalkyl, $C_5$-$C_{20}$ polyhydroxyaryl, $C_1$-$C_{10}$ aminoalkyl, —$CH_2$($CH_2OCH_2$)$_b$—$CH_2$—OH, —($CH_2$)$_a$—$CO_2$H, —($CH_2$)$_a$—CONH-Bm, —$CH_2$—($CH_2OCH_2$)$_b$—$CH_2$—CONH-Bm, —($CH_2$)$_a$—NHCO-Bm, —$CH_2$—($CH_2OCH_2$)$_b$—$CH_2$—NHCO-Bm, —($CH_2$)$_a$—N($R^3$)—($CH_2$)$_b$—CONH-Bm, ($CH_2$)$_a$—N($R^3$)—($CH_2$)$_c$—NHCO-Bm, —($CH_2$)$_a$—N($R^3$)—$CH_2$—($CH_2OCH_2$)$_b$—$CH_2$—CONH-Bm, —($CH_2$)$_a$—N($R^3$)—$CH_2$—($CH_2OCH_2$)$_b$—$CH_2$—NHCO-Bm, —$CH_2$—($CH_2OCH_2$)$_b$—$CH_2$—N($R^3$)—($CH_2$)$_a$—CONH-Bm, —$CH_2$—($CH_2OCH_2$)$_b$—$CH_2$—N($R^3$)—($CH_2$)$_a$—NHCO-Bm, —$CH_2$—($CH_2OCH_2$)$_b$—$CH_2$—N($R^3$)—$CH_2$—($CH_2OCH_2$)$_d$—CONH-Bm, —$CH_2$—($CH_2OCH_2$)$_b$—$CH_2$—N($R^3$)—$CH_2$—($CH_2OCH_2$)$_d$—NHCO-Bm, —($CH_2$)$_a$—$NR^3R^4$, and —$CH_2$($CH_2OCH_2$)$_b$—$CH_2NR^3R^4$; $Z^5$ is selected from the group consisting of hydrogen, $C_1$-$C_{10}$ alkyl, $C_5$-$C_{20}$ aryl, $C_1$-$C_{10}$ alkoxyl, $C_1$-$C_{10}$ polyalkoxyalkyl, $C_1$-$C_{20}$ polyhydroxyalkyl, $C_5$-$C_{20}$ polyhydroxyaryl, $C_1$-$C_{10}$ aminoalkyl, —$CH_2$($CH_2OCH_2$)$_b$—$CH_2$—OH, —($CH_2$)$_a$—$CO_2$H, —($CH_2$)$_a$—CONH-Dm, —$CH_2$—($CH_2OCH_2$)$_b$—$CH_2$—CONH-Dm, —($CH_2$)$_a$—NHCO-Dm, —$CH_2$—($CH_2OCH_2$)$_b$—$CH_2$—NHCO-Dm, —($CH_2$)$_a$—N($R^3$)—($CH_2$)$_b$—CONH-Dm, ($CH_2$)$_a$—N($R^3$)—($CH_2$)$_c$—NHCO-Dm, —($CH_2$)$_a$—N($R^3$)—$CH_2$—($CH_2OCH_2$)$_b$—$CH_2$—CONH-Dm, —($CH_2$)$_a$—N($R^3$)—$CH_2$—($CH_2OCH_2$)$_b$—

CH$_2$—NHCO-Dm, —CH$_2$—(CH$_2$OCH$_2$)$_b$—CH$_2$—N(R$^3$)—(CH$_2$)$_a$—CONH-Dm, —CH$_2$—(CH$_2$OCH$_2$)$_b$—CH$_2$—N(R$^3$)—(CH$_2$)$_a$—NHCO-Dm, —CH$_2$—(CH$_2$OCH$_2$)$_b$—CH$_2$—N(R$^3$)—CH$_2$—(CH$_2$OCH$_2$)$_d$—CONH-Dm, —CH$_2$—(CH$_2$OCH$_2$)$_b$—CH$_2$—N(R$^3$)—CH$_2$—(CH$_2$OCH$_2$)$_d$—NHCO-Dm, —(CH$_2$)$_a$—NR$^3$R$^4$, and —CH$_2$(CH$_2$OCH$_2$)$_b$—CH$_2$NR$^3$R$^4$; A$_3$ is a single or a double bond; B$_3$, C$_3$, and D$_3$ may be the same or different and are selected from the group consisting of —O—, —S—, —Se—, —P—, —CR$^1$R$^2$, —CR$^1$, alkyl, NR$^3$, and —C=O; A$_3$, B$_3$, C$_3$, and D$_3$ may together form a 6- to 12-membered carbocyclic ring or a 6- to 12-membered heterocyclic ring optionally containing one or more oxygen, nitrogen, or sulfur atom; a$_5$ is independently from 0 to 5; R$^1$ to R$^4$, and R$^{58}$ to R$^{66}$ are independently selected from the group consisting of hydrogen, C$_1$-C$_{10}$ alkyl, C$_5$-C$_{20}$ aryl, C$_1$-C$_{10}$ alkoxyl, C$_1$-C$_{10}$ polyalkoxyalkyl, C$_1$-C$_{20}$ polyhydroxyalkyl, C$_5$-C$_{20}$ polyhydroxyaryl, C$_1$-C$_{10}$ aminoalkyl, glucose derivatives of R groups, cyano, nitro, halogen, saccharide, peptide, —CH$_2$(CH$_2$OCH$_2$)$_b$—CH$_2$—OH, —(CH$_2$)$_a$—CO$_2$H, —(CH$_2$)$_a$—CONH-Bm, —CH$_2$—(CH$_2$OCH$_2$)$_b$—CH$_2$—CONH-Bm, —(CH$_2$)$_a$—NHCO-Bm, —CH$_2$—(CH$_2$OCH$_2$)$_b$—CH$_2$—NHCO-Bm, —(CH$_2$)$_a$—OH and —CH$_2$—(CH$_2$OCH$_2$)$_b$—CO$_2$H; Bm and Dm are independently selected from the group consisting of a peptide, a protein, a cell, an antibody, an antibody fragment, a saccharide, a glycopeptide, a peptidomimetic, a drug, a drug mimic, a hormone, a metal chelating agent, a radioactive or nonradioactive metal complex, a photosensitizer for phototherapy, and an echogenic agent; a and c are independently from 1 to 20; and b and d are independently from 1 to 100.

Still yet another aspect of the present invention is directed to a composition including an indocyanine dye of general formula 6

—CH$_2$—N(R$^3$)—CH$_2$—(CH$_2$OCH$_2$)$_d$—NHCO-Bm, —(CH$_2$)$_a$—NR$^3$R$^4$, and —CH$_2$(CH$_2$OCH$_2$)$_b$—CH$_2$NR$^3$R$^4$; Z$^6$ is selected from the group consisting of hydrogen, C$_1$-C$_{10}$ alkyl, C$_5$-C$_{20}$ aryl, C$_1$-C$_{10}$ alkoxyl, C$_1$-C$_{10}$ polyalkoxyalkyl, C$_1$-C$_{20}$ polyhydroxyalkyl, C$_5$-C$_{20}$ polyhydroxyaryl, C$_1$-C$_{10}$ aminoalkyl, —CH$_2$(CH$_2$OCH$_2$)$_b$—CH$_2$—OH, —(CH$_2$)$_a$—CO$_2$H —(CH$_2$)$_a$—CONH-Dm, —CH$_2$—(CH$_2$OCH$_2$)$_b$—CH$_2$—CONH-Dm, —(CH$_2$)$_a$—NHCO-Dm, —CH$_2$—(CH$_2$OCH$_2$)$_b$—CH$_2$—NHCO-Dm, —(CH$_2$)$_a$—N(R$^3$)—(CH$_2$)$_b$—CONH-Dm, (CH$_2$)$_a$—N(R$^3$)—(CH$_2$)$_c$—NHCO-Dm, —(CH$_2$)$_a$—N(R$^3$)—CH$_2$—(CH$_2$OCH$_2$)$_b$—CH$_2$—CONH-Dm, —(CH$_2$)$_a$—N(R$^3$)—CH$_2$—(CH$_2$OCH$_2$)$_b$—CH$_2$—NHCO-Dm, —CH$_2$—(CH$_2$OCH$_2$)$_b$—CH$_2$—N(R$^3$)—(CH$_2$)$_a$—CONH-Dm, —CH$_2$—(CH$_2$OCH$_2$)$_b$—CH$_2$—N(R$^3$)—(CH$_2$)$_a$—NHCO-Dm, —CH$_2$—(CH$_2$OCH$_2$)$_b$—CH$_2$—N(R$^3$)—CH$_2$—(CH$_2$OCH$_2$)$_d$—CONH-Dm, —CH$_2$—(CH$_2$OCH$_2$)$_b$—CH$_2$—N(R$^3$)—CH$_2$—(CH$_2$OCH$_2$)$_d$—NHCO-Dm, —(CH$_2$)$_a$—NR$^3$R$^4$, and —CH$_2$(CH$_2$OCH$_2$)$_b$—CH$_2$NR$^3$R$^4$; A$_4$ is a single or a double bond; B$_4$, C$_4$, and D$_4$ may be the same or different and are selected from the group consisting of —O—, —S—, —Se—; —P—, —CR$^1$R$^2$, —CR$^1$, alkyl, NR$^3$, and —C=O; A$_4$, B$_4$, C$_4$, and D$_4$ may together form a 6- to 12-membered carbocyclic ring or a 6- to 12-membered heterocyclic ring optionally containing one or more oxygen, nitrogen, or sulfur atom; a$_6$ is independently from 0 to 5; R$^1$ to R$^4$, and R$^{67}$ to R$^{79}$ are independently selected from the group consisting of hydrogen, C$_1$-C$_{10}$ alkyl, C$_5$-C$_{20}$ aryl, C$_1$-C$_{10}$ alkoxyl, C$_1$-C$_{10}$ polyalkoxyalkyl, C$_1$-C$_{20}$ polyhydroxyalkyl, C$_5$-C$_{20}$ polyhydroxyaryl, C$_1$-C$_{10}$ aminoalkyl, glucose derivatives of R groups, cyano, nitro, halogen, saccharide, peptide, —CH$_2$(CH$_2$OCH$_2$)$_b$—CH$_2$—OH, —(CH$_2$)$_a$—CO$_2$H, —(CH$_2$)$_a$—CONH-Bm, —CH$_2$—(CH$_2$OCH$_2$)$_b$—CH$_2$—CONH-Bm,

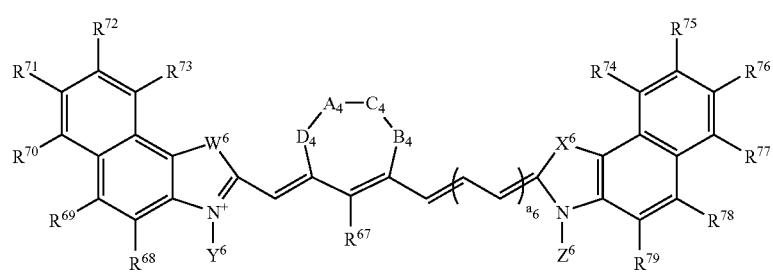

Formula 6 wherein W$^6$ and X$^6$ may be the same or different and are selected from the group consisting of —CR$^1$R$^2$, —O—, —NR$^3$, —S—, and —Se; Y$^6$ is selected from the group consisting of hydrogen, C$_1$-C$_{10}$ alkyl, C$_5$-C$_{20}$ aryl, C$_1$-C$_{10}$ alkoxyl, C$_1$-C$_{10}$ polyalkoxyalkyl, C$_1$-C$_{20}$ polyhydroxyalkyl, C$_5$-C$_{20}$ polyhydroxyaryl, C$_1$-C$_{10}$ aminoalkyl, —CH$_2$(CH$_2$OCH$_2$)$_b$—CH$_2$—OH, —(CH$_2$)$_a$—CO$_2$H, —(CH$_2$)$_a$—CONH-Bm, —CH$_2$—(CH$_2$OCH$_2$)$_b$—CH$_2$—CONH-Bm, —(CH$_2$)$_a$—NHCO-Bm, —CH$_2$—(CH$_2$OCH$_2$)$_b$—CH$_2$—NHCO-Bm, —(CH$_2$)$_a$—N(R$^3$)—(CH$_2$)$_b$—CONH-Bm, (CH$_2$)$_a$—N(R$^3$)—(CH$_2$)$_c$—NHCO-Bm, —(CH$_2$)$_a$—N(R$^3$)—CH$_2$—(CH$_2$OCH$_2$)$_b$—CH$_2$—CONH-Bm, —(CH$_2$)$_a$—N(R$^3$)—CH$_2$—(CH$_2$OCH$_2$)$_b$—CH$_2$—NHCO-Bm, —CH$_2$—(CH$_2$OCH$_2$)$_b$—CH$_2$—N(R$^3$)—(CH$_2$)$_a$—CONH-Bm, —CH$_2$—(CH$_2$OCH$_2$)$_b$—CH$_2$—N(R$^3$)—(CH$_2$)$_a$—NHCO-Bm, —CH$_2$—(CH$_2$OCH$_2$)$_b$—CH$_2$—N(R$^3$)—CH$_2$—(CH$_2$OCH$_2$)$_d$—CONH-Bm, —CH$_2$—(CH$_2$OCH$_2$)$_b$ —(CH$_2$)$_a$—NHCO-Bm, —CH$_2$—(CH$_2$OCH$_2$)$_b$—CH$_2$—NHCO-Bm, —(CH$_2$)$_a$—OH or —CH$_2$—(CH$_2$OCH$_2$)$_b$—CO$_2$H; Bm and Dm are independently selected from the group consisting of a peptide, a protein, a cell, an antibody, an antibody fragment, a saccharide, a glycopeptide, a peptidomimetic, a drug, a drug mimic, a hormone, a metal chelating agent, a radioactive or nonradioactive metal complex, a photosensitizer for phototherapy, and an echogenic agent; a and c are independently from 1 to 20; and b and d are independently from 1 to 100.

A chelate such as ethylenediaminetetraacetic acid (EDTA), diethylenetriaminepentaacetic acid (DPTA), 1,4,7,10 tetraazacyclododecane-tetraacetic acid (DOTA), or their derivatives, can be attached to the compounds of Formulas 1-6 as one or more R groups. These structures are expected to be highly water soluble.

The invention will be further appreciated in light of the following figures, detailed description, and examples.

BRIEF DESCRIPTION OF THE FIGURES

The file of U.S. patent application Ser. No. 10/800,531 (filed Mar. 15, 2004), which is hereby incorporated by reference, contains color versions of FIGS. 7A-11 below. Copies of that patent application with color drawing(s) may be provided by the Patent and Trademark Office upon request and payment of the necessary fee.

DETAILED DESCRIPTION OF THE INVENTION

The dyes of formulas 1 to 6 as compounds, compositions, and in methods of imaging offer significant advantages over conventional dyes known in the art. These inventive dyes form starburst dendrimers which prevent aggregation in solution by preventing intramolecular and intermolecular ordered hydrophobic interactions, and have multiple attachment sites proximal to the dye chromophore for ease of forming bioactive molecules. The presence of rigid and extended chromophore backbone enhances their fluorescence quantum yield and extends their maximum absorption beyond 800 nm. Conjugation of biomolecules to these dyes is readily achievable.

The inventive bioconjugates of the present invention also exploit the symmetric nature of the cyanine and indocyanine dye structures by incorporating one to ten receptor-targeting groups in close proximity to each other, such that the receptor binding can be greatly enhanced due to a cooperative effect. Accordingly, several cyanine dyes containing one or more targeting domains have been prepared and tested in vivo for biological activity.

The inventive dye-bioconjugates of formulas 1 to 6 are useful for various biomedical applications. These include, but are not limited to, tomographic imaging of organs, monitoring of organ functions, coronary angiography, fluorescence endoscopy, detection, imaging, and therapy of tumors, laser guided surgery, photoacoustic methods, and sonofluorescent methods.

Specific embodiments to accomplish some of the aforementioned biomedical applications are given below. The dyes of the present invention are prepared according to methods well known in the art as illustrated in the exemplary synthetic schemes of FIGS. 1-5.

Figure 1:
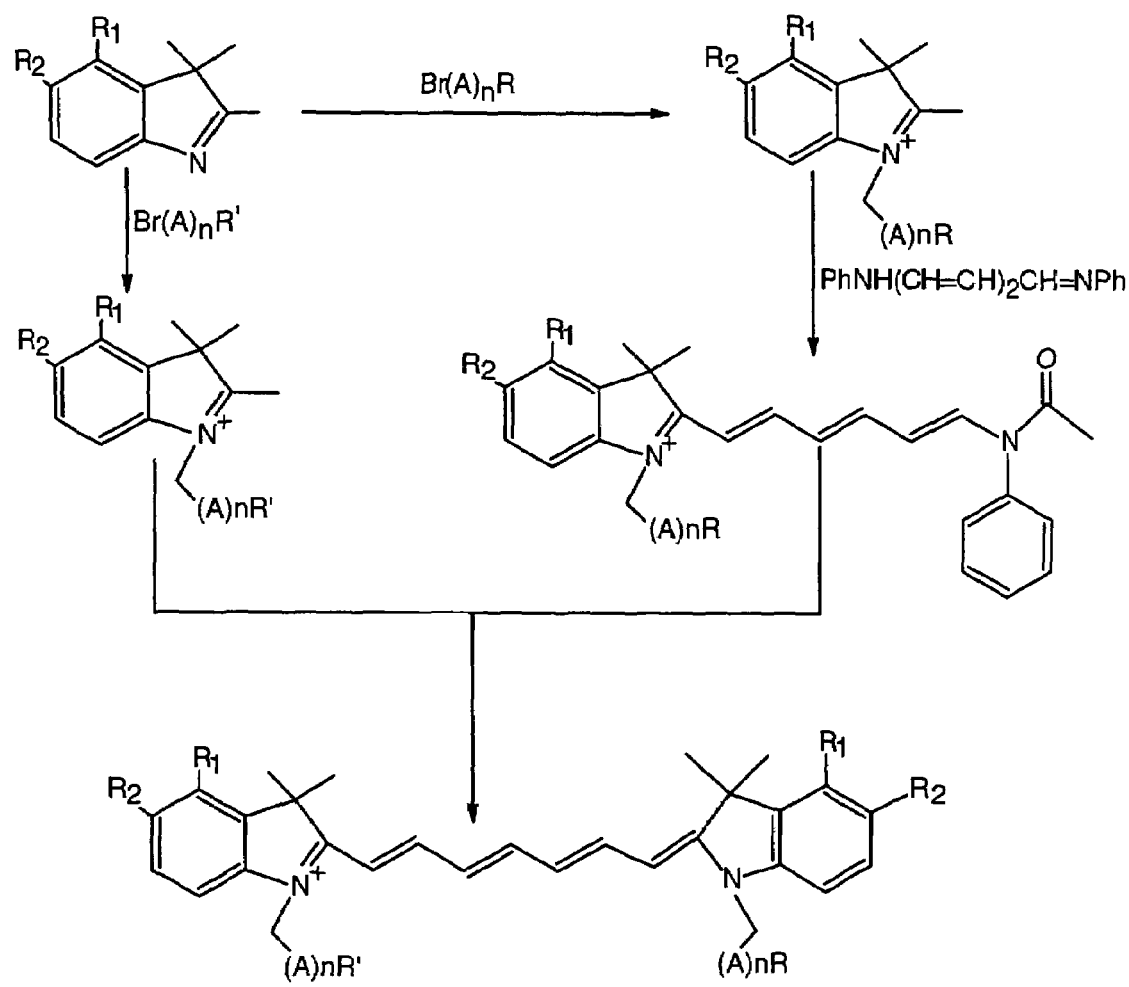
FIG. 1 shows the reaction pathway for the synthesis of bis-carboxylic acid cyanine dyes.

FIG. 1 illustrates the synthetic scheme for bis-carboxylic acid cyanine dyes, where A=$CH_2$ or $CH_2OCH_2$; R=COOH; R'=COOH, NHFmoc; $CO_2$t-Bu; $SO_3^-$; $R_1$=$R_2$=H (Formula 1) or $R_1$, $R_2$=fused phenyl (Formula 2).

Figure 2:
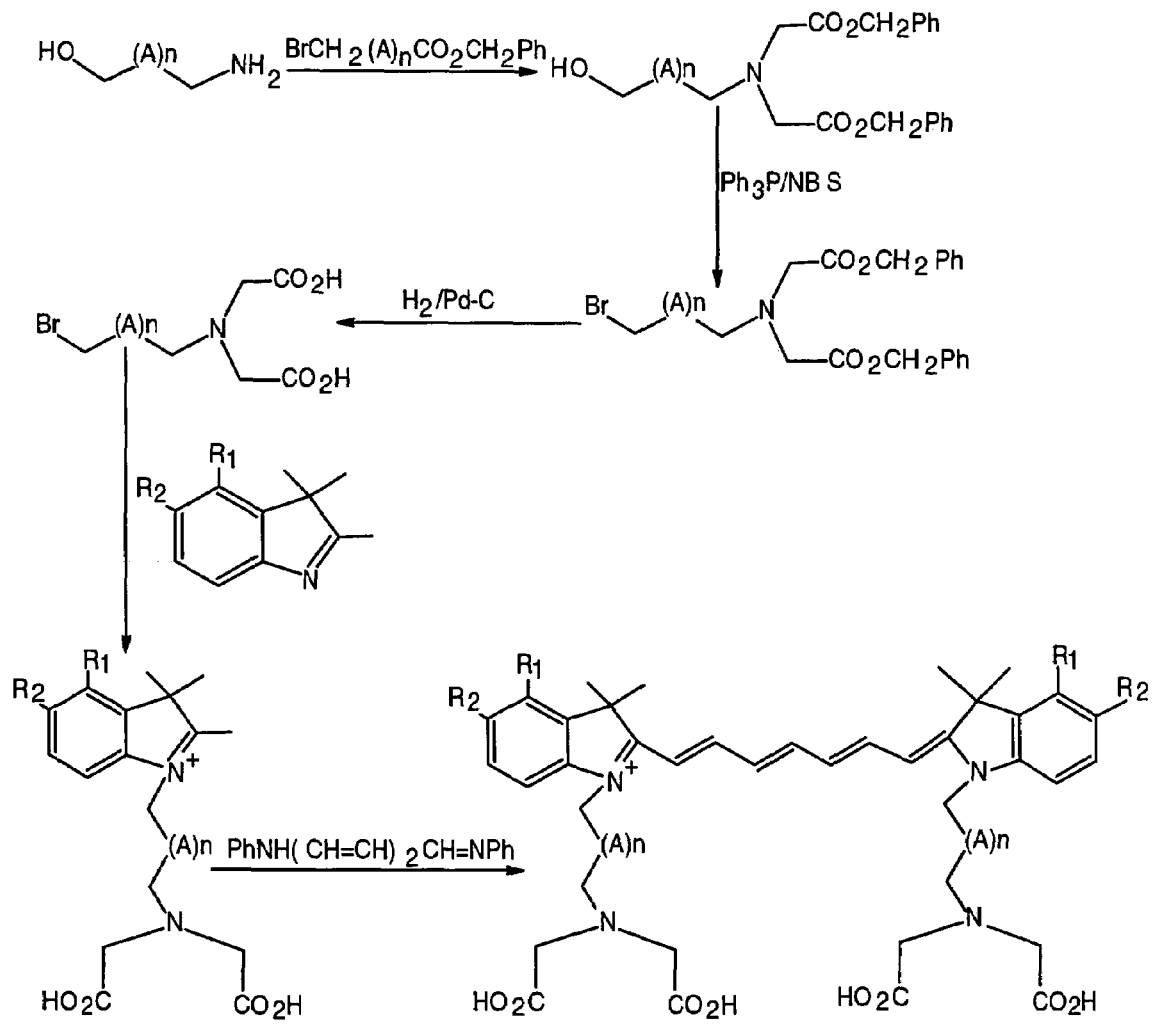
FIG. 2 shows the reaction pathway for the synthesis of tetracarboxylic acid cyanine dyes.

FIG. 2 illustrates the synthetic scheme for tetracarboxylic acid cyanine dyes, where A=$CH_2$ or $CH_2OCH_2$; $R_1$=$R_2$=H (Formula 1) or $R_1$, $R_2$=fused phenyl (Formula 2).

Figure 3:
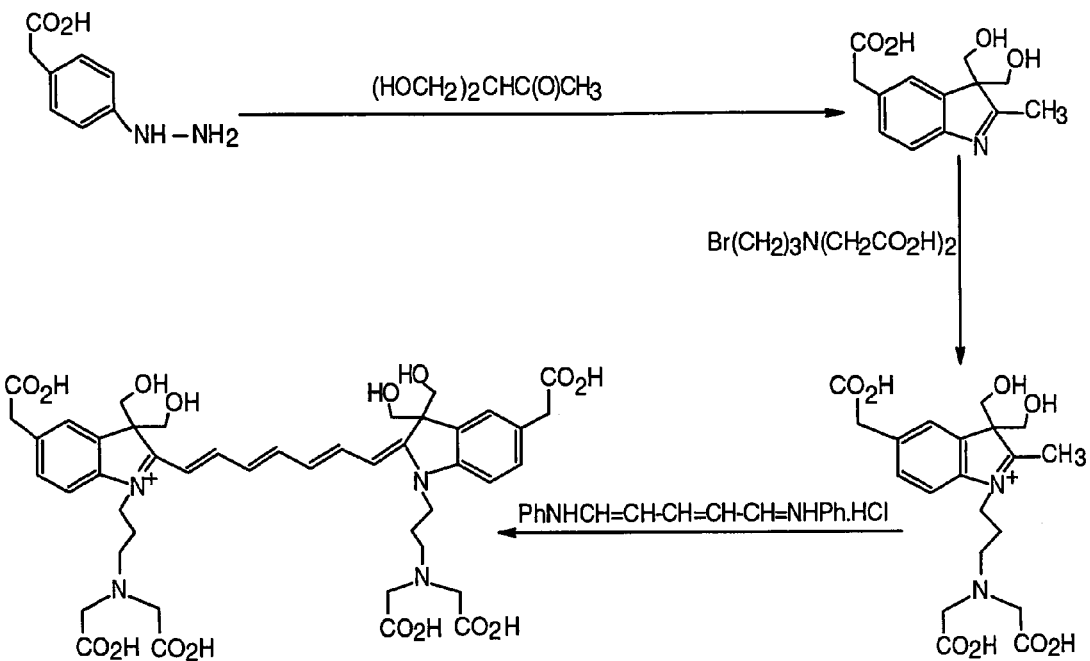
FIG. 3 shows the reaction pathway for the synthesis of polyhydroxycarboxylic acid dyes.

FIG. 3 illustrates the synthetic scheme for polyhydroxy-carboxylic acid cyanine dyes.

Figure 4:
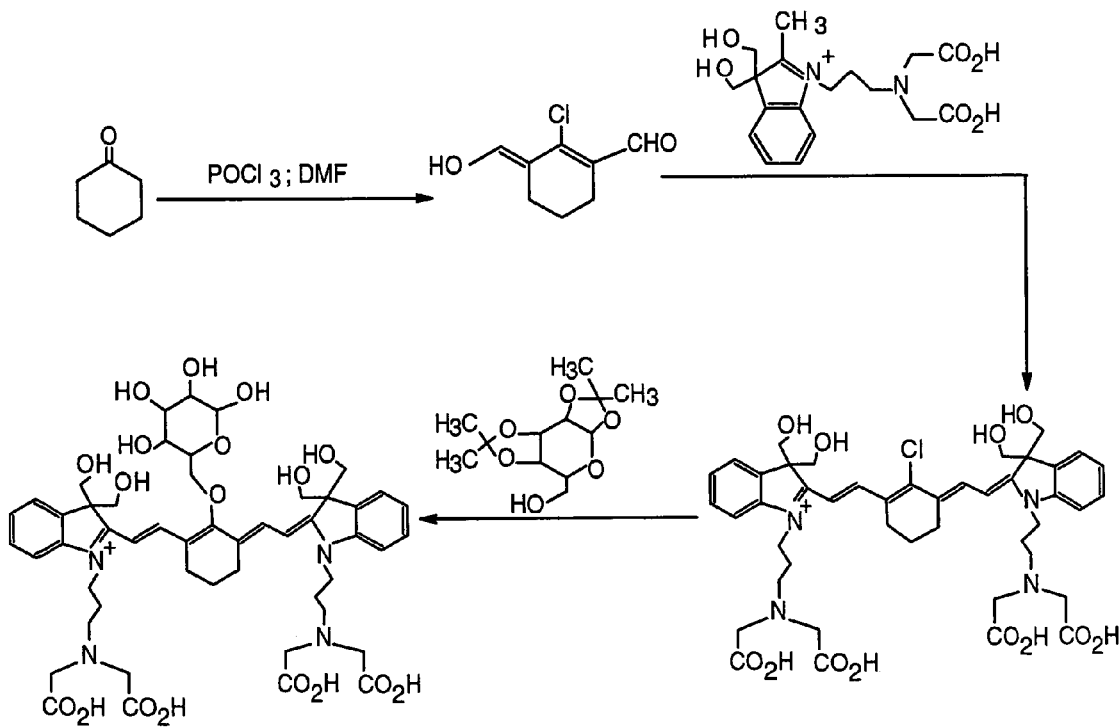
FIG. 4 shows the reaction pathway for the synthesis of non-aggregating cyanine dyes.

FIG. 4 illustrates the synthetic scheme for non-aggregating cyanine dyes.

Figure 5:
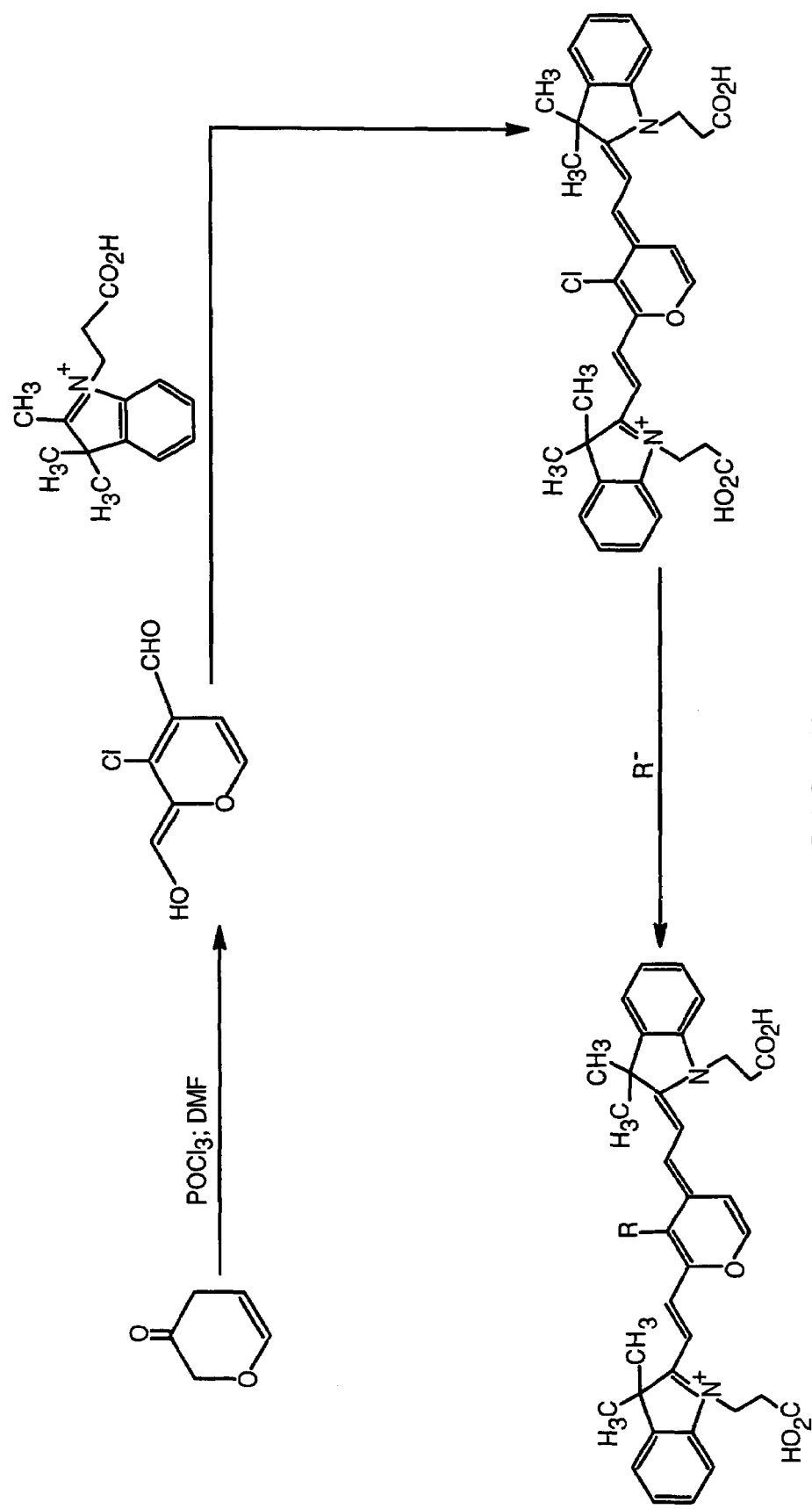
FIG. 5 shows the reaction pathway for the synthesis of long wavelength absorbing dyes.

FIG. 5 illustrates the synthetic scheme for long wavelength-absorbing tunable cyanine dyes.

In one aspect, dyes of the invention have the Formula 1, wherein $W^1$ and $X^1$ may be the same or different and are selected from the group consisting of —$CR^wR^x$, —O—, —$NR^y$, —S—, and —Se—; $Q^2$ is a single bond or is selected from the group consisting of —O—, —S—, —Se—, and —$NR^5$; $a_1$ and $b_1$ independently vary from 0 to 5; a and c are independently from 1 to 20; b and d are independently from 1 to 100; $Y^1$ is a constituent selected from the group consisting of hydrogen, $C_1$-$C_{10}$ alkyl, $C_5$-$C_{20}$ aryl, $C_1$-$C_{10}$ alkoxyl, $C_1$-$C_{10}$ polyalkoxyalkyl, $C_1$-$C_{20}$ polyhydroxyalkyl, $C_5$-$C_{20}$ polyhydroxyaryl, $C_1$-$C_{10}$ aminoalkyl, —$CH_2(CH_2OCH_2)_b$— —$CH_2$—OH, —$(CH_2)_a$—$CO_2H$, —$(CH_2)_a$—CONH-Bm, —$CH_2$—$(CH_2OCH_2)_b$—$CH_2$—CONH-Bm, —$(CH_2)_a$—NHCO-Bm, —$CH_2$—$(CH_2OCH_2)_b$—$CH_2$—NHCO-Bm, —$(CH_2)_a$—N($R^y$)—$(CH_2)_b$—CONH-Bm, —$(CH_2)_a$—N($R^y$)—$CH_2$—$(CH_2OCH_2)_c$—NHCO-Bm, —$(CH_2)_a$—N($R^y$)—$CH_2$—$(CH_2OCH_2)_b$—$CH_2$—CONH-Bm, —$(CH_2)_a$—N($R^y$)—$CH_2$—$(CH_2OCH_2)_b$—$CH_2$—NHCO-Bm, —$CH_2$—$(CH_2OCH_2)_b$—$CH_2$—N($R^y$)—$(CH_2)_a$—CONH-Bm, —$CH_2$—$(CH_2OCH_2)_b$—$CH_2$—N($R^y$)—$(CH_2)_a$—NHCO-Bm, —$CH_2$—$(CH_2OCH_2)_b$—$CH_2$—N($R^y$)—$CH_2$—$(CH_2OCH_2)_d$—CONH-Bm, —$CH_2$—$(CH_2OCH_2)_b$—$CH_2$—N($R^y$)—$CH_2$—$(CH_2OCH_2)_d$—NHCO-Bm, —$(CH_2)_a$—$NR^yR^z$, and —$CH_2(CH_2OCH_2)_b$—$CH_2NR^yR^z$; $Z^1$ is a constituent selected from the group consisting of hydrogen, $C_1$-$C_{10}$ alkyl, $C_5$-$C_{20}$ aryl, $C_1$-$C_{10}$ alkoxyl, $C_1$-$C_{10}$ polyalkoxyalkyl, $C_1$-$C_{20}$ polyhydroxyalkyl, $C_5$-$C_{20}$ polyhydroxyaryl, $C_1$-$C_{10}$ aminoalkyl, —$CH_2(CH_2OCH_2)_b$—$CH_2$—OH, —$(CH_2)_a$—$CO_2H$, —$(CH_2)_a$—CONH-Dm, —$CH_2$—$(CH_2OCH_2)_b$—$CH_2$—CONH-Dm, —$(CH_2)_a$—NHCO-Dm, —$CH_2$—$(CH_2OCH_2)_b$—$CH_2$—NHCO-Dm, —$(CH_2)_a$—N($R^y$)—$(CH_2)_b$—CONH-Dm, —$(CH_2)_a$—N($R^y$)—$CH_2$—$(CH_2OCH_2)_c$—NHCO-Dm, —$(CH_2)_a$—N($R^y$)—$CH_2$—$(CH_2OCH_2)_b$—$CH_2$—CON H-Dm, —$(CH_2)_a$—N($R^y$)—$CH_2$—$(CH_2OCH_2)_b$—$CH_2$—NHCO-Dm, —$CH_2$—$(CH_2OCH_2)_b$—$CH_2$—N($R^y$)—$(CH_2)_a$—CONH-Dm, —$CH_2$—$(CH_2OCH_2)_b$—$CH_2$—N($R^y$)—$(CH_2)_a$—NHCO-Dm, —$CH_2$—$(CH_2OCH_2)_b$—$CH_2$—N($R^y$)—$CH_2$—$(CH_2OCH_2)_d$—CONH-Dm, —$CH_2$—$(CH_2OCH_2)_b$—$CH_2$ —N(R$^y$)—CH$_2$—(CH$_2$OCH$_2$)$_d$—NHCO-Dm, —(CH$_2$)$_a$—NR$^y$R$^z$, and —CH$_2$(CH$_2$OCH$_2$)$_b$—CH$_2$NR$^y$R$^z$; R$^w$, R$^x$, R$^y$, R$^z$, and R$^1$ to R$^9$ are independently selected from the group consisting of hydrogen, C$_1$-C$_{10}$ alkyl, C$_5$-C$_{20}$ aryl, C$_1$-C$_{10}$ alkoxyl, C$_1$-C$_{10}$ polyalkoxyalkyl, C$_1$-C$_{20}$ polyhydroxyalkyl, C$_5$-C$_{20}$ polyhydroxyaryl, C$_1$-C$_{10}$ aminoalkyl, glucose derivatives of R groups, cyano, nitro, halogen, saccharide, peptide, —CH$_2$(CH$_2$OCH$_2$)$_b$—CH$_2$—OH, —(CH$_2$)$_a$—CO$_2$H, —(CH$_2$)$_a$—CONH-Bm, —CH$_2$—(CH$_2$OCH$_2$)$_b$—CH$_2$—CONH-Bm, —(CH$_2$)$_a$—NHCO-Bm, —CH$_2$—(CH$_2$OCH$_2$)$_b$—CH$_2$—NHCO-Bm, —(CH$_2$)$_a$—OH and —CH$_2$—(CH$_2$OCH$_2$)$_b$—CO$_2$H; and Bm and Dm are independently selected from the group consisting of a peptide, a protein, a cell, an antibody, an antibody fragment, a saccharide, a glycopeptide, a peptidomimetic, a drug, a drug mimic, a hormone, a metal chelating agent, a radioactive or nonradioactive metal complex, a photosensitizer for phototherapy, and an echogenic agent.

With regard to preferred cyanine dyes of Formula 1, at least one of Y$^1$, Z$^1$, R$^w$, R$^x$, R$^y$, R$^z$, R$^1$, R$^2$, R$^3$, R$^4$, R$^5$, R$^6$, R$^7$, R$^8$ and R$^9$ is preferably a constituent including Bm or Dm. Further, it is preferred that at least one Bm or Dm of the dye of Formula 1 is selected from the group consisting of a peptide, a protein, a cell, a metal chelating agent, a radioactive or nonradioactive metal complex, a photosensitizer for phototherapy, and an echogenic agent. For instance, in one preferred family of embodiments, at least one of Y$^1$, Z$^1$, R$^w$, R$^x$, R$^y$, R$^z$, R$^1$, R$^2$, R$^3$, R$^4$, R$^5$, R$^6$, R$^7$, R$^8$ and R$^9$ is a constituent including Bm or Dm, and at least one of Bm and Dm is a peptide such as Octreotide, Octreotate, Bombesin, Cholecystokinin, or Neurotensin.

In another family of preferred embodiments of the dyes of Formula 1, at least one of Y$^1$, Z$^1$, R$^w$, R$^x$, R$^y$, R$^z$, R$^1$, R$^2$, R$^3$, R$^4$, R$^5$, R$^6$, R$^7$, R$^8$ and R$^9$ is a constituent including Bm or Dm, and at least one of Bm and Dm is a photosensitizer for phototherapy. For example, in one preferred embodiment, at least one of Y$^1$, R$^w$, R$^x$, R$^y$, R$^z$, R$^1$, R$^2$, R$^3$, R$^4$, R$^5$, R$^6$, R$^7$, R$^8$ and R$^9$ is a constituent including Bm, and Z$^1$ is a constituent including Dm. In such a preferred embodiment, one of Bm and Dm is a peptide, and the other of Bm and Dm is a photosensitizer for phototherapy.

In still another family of preferred embodiments of the dyes of Formula 1, at least one of Y$^1$, Z$^1$, R$^w$, R$^x$, R$^y$, R$^z$, R$^1$, R$^2$, R$^3$, R$^4$, R$^5$, R$^6$, R$^7$, R$^8$ and R$^9$ is a constituent including Bm or Dm. However, in this preferred family, Bm and/or Dm is selected from the group consisting of a protein, a cell, a metal chelating agent, a radioactive or nonradioactive metal complex, a photosensitizer for phototherapy, and an echogenic agent.

Turning to a second aspect of the invention, some indocyanine dyes of the invention have the Formula 2, wherein W$^2$ and X$^2$ may be the same or different and are selected from the group consisting of —CR$^1$R$^2$, —O—, —NR$^3$, —S—, and —Se—; Q$^2$ is a single bond or is selected from the group consisting of —O—, —S—, —Se—, and —NR$^5$; a$_2$ and b$_2$ independently vary from 0 to 5; a and c are independently from 1 to 20; b and d are independently from 1 to 100; Y$^2$ is selected from the group consisting of hydrogen, C$_1$-C$_{10}$ alkyl, C$_5$-C$_{20}$ aryl, C$_1$-C$_{10}$ alkoxyl, C$_1$-C$_{10}$ polyalkoxyalkyl, C$_1$-C$_{20}$ polyhydroxyalkyl, C$_5$-C$_{20}$ polyhydroxyaryl, C$_1$-C$_{10}$ aminoalkyl, —CH$_2$(CH$_2$OCH$_2$)$_b$—CH$_2$—OH, —(CH$_2$)$_a$—CO$_2$H, —(CH$_2$)$_a$—CONH-Bm, —CH$_2$—(CH$_2$OCH$_2$)$_b$—CH$_2$—CONH-Bm, —(CH$_2$)$_a$—NHCO-Bm, —CH$_2$—(CH$_2$OCH$_2$)$_b$—CH$_2$—NHCO-Bm, —(CH$_2$)$_a$—N(R$^3$)—(CH$_2$)$_b$—CONH-Bm, —(CH$_2$)$_a$—N(R$^3$)—(CH$_2$)$_c$—NHCO-Bm, —(CH$_2$)$_a$—N(R$^3$)—CH$_2$—(CH$_2$OCH$_2$)$_b$—CH$_2$—CONH-Bm, —(CH$_2$)$_a$—N(R$^3$)—CH$_2$—(CH$_2$OCH$_2$)$_b$—CH$_2$—NHCO-Bm, —CH$_2$—(CH$_2$OCH$_2$)$_b$—CH$_2$—N(R$^3$)—(CH$_2$)$_a$—CONH-Bm, —CH$_2$—(CH$_2$OCH$_2$)$_b$—CH$_2$—N(R$^3$)—(CH$_2$)$_a$—NHCO-Bm, —CH$_2$—(CH$_2$OCH$_2$)$_b$—CH$_2$—N(R$^3$)—CH$_2$—(CH$_2$OCH$_2$)$_d$—CONH-Bm, —CH$_2$—(CH$_2$OCH$_2$)$_b$—CH$_2$—N(R$^3$)—CH$_2$—(CH$_2$OCH$_2$)$_d$—NHCO-Bm, —(CH$_2$)$_a$—NR$^3$R$^4$, and —CH$_2$(CH$_2$OCH$_2$)$_b$—CH$_2$NR$^3$R$^4$; Z$^2$ is selected from the group consisting of hydrogen, C$_1$-C$_{10}$ alkyl, C$_5$-C$_{20}$ aryl, C$_1$-C$_{10}$ alkoxyl, C$_1$-C$_{10}$ polyalkoxyalkyl, C$_1$-C$_{20}$ polyhydroxyalkyl, C$_5$-C$_{20}$ polyhydroxyaryl, C$_1$-C$_{10}$ aminoalkyl, —CH$_2$(CH$_2$OCH$_2$)$_b$—CH$_2$—OH, —(CH$_2$)$_a$—CO$_2$H, —(CH$_2$)$_a$—CONH-Dm, —CH$_2$—(CH$_2$OCH$_2$)$_b$—CH$_2$—CONH-Dm, —(CH$_2$)$_a$—NHCO-Dm, —CH$_2$—(CH$_2$OCH$_2$)$_b$—CH$_2$—NHCO-Dm, —(CH$_2$)$_a$—N(R$^3$)—(CH$_2$)$_b$—CONH-Dm, (CH$_2$)$_a$—N(R$^3$)—(CH$_2$)$_c$—NHCO-Dm, —(CH$_2$)$_a$—N(R$^3$)—CH$_2$—(CH$_2$OCH$_2$)$_b$—CH$_2$—CONH-Dm, —(CH$_2$)$_a$—N(R$^3$)—CH$_2$—(CH$_2$OCH$_2$)$_b$—CH$_2$—NHCO-Dm, —CH$_2$—(CH$_2$OCH$_2$)$_b$—CH$_2$—N(R$^3$)—(CH$_2$)$_a$—CONH-Dm, —CH$_2$—(CH$_2$OCH$_2$)$_b$—CH$_2$—N(R$^3$)—(CH$_2$)$_a$—NHCO-Dm, —CH$_2$—(CH$_2$OCH$_2$)$_b$—CH$_2$—N(R$^3$)—CH$_2$—(CH$_2$OCH$_2$)$_d$—CONH-Dm, —CH$_2$—(CH$_2$OCH$_2$)$_b$—CH$_2$—N(R$^3$)—CH$_2$—(CH$_2$OCH$_2$)$_d$—NHCO-Dm, —(CH$_2$)$_a$—NR$^3$R$^4$, and —CH$_2$(CH$_2$OCH$_2$)$_b$—CH$_2$NR$^3$R$^4$; R$^1$ to R$^5$, and R$^{16}$ to R$^{28}$ are constituents independently selected from the group consisting of hydrogen, C$_1$-C$_{10}$ alkyl, C$_5$-C$_{20}$ aryl, C$_1$-C$_{10}$ alkoxyl, C$_1$-C$_{10}$ polyalkoxyalkyl, C$_1$-C$_{20}$ polyhydroxyalkyl, C$_5$-C$_{20}$ polyhydroxyaryl, C$_1$-C$_{10}$ aminoalkyl, glucose derivatives of R groups, cyano, nitro, halogen, saccharide, peptide, —CH$_2$(CH$_2$OCH$_2$)$_b$—CH$_2$—OH, —(CH$_2$)$_a$—CO$_2$H, —(CH$_2$)$_a$—CONH-Bm, —CH$_2$—(CH$_2$OCH$_2$)$_b$—CH$_2$—CONH-Bm, —(CH$_2$)$_a$—NHCO-Bm, —CH$_2$—(CH$_2$OCH$_2$)$_b$—CH$_2$—NHCO-Bm, —(CH$_2$)$_a$—OH and —CH$_2$—(CH$_2$OCH$_2$)$_b$—CO$_2$H; and Bm and Dm are independently selected from the group consisting of a peptide, a protein, a cell, an antibody, an antibody fragment, a saccharide, a glycopeptide, a peptidomimetic, a drug, a drug mimic, a hormone, a metal chelating agent, a radioactive or nonradioactive metal complex, a photosensitizer for phototherapy, and an echogenic agent.

With regard to preferred indocyanine dyes of Formula 2, at least one of Y$^2$, Z$^2$, R$^1$, R$^2$, R$^3$, R$^4$, R$^5$, R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$ and R$^{28}$ is a constituent including Bm or Dm. Further, it is preferred that at least one Bm or Dm of the indocyanine dye is selected from the group consisting of a peptide, a protein, a cell, a metal chelating agent, a radioactive or nonradioactive metal complex, a photosensitizer for phototherapy, and an echogenic agent. For instance, in one preferred family of embodiments, at least one of Y$^2$, Z$^2$, R$^1$, R$^2$, R$^3$, R$^4$, R$^5$, R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$ and R$^{28}$ is a constituent including Bm or Dm, and at least one of Bm and Dm is a peptide such as Octreotide, Octreotate, Bombesin, Cholecystokinin, or Neurotensin.

In another family of preferred embodiments of the dyes of Formula 2, at least one of Y$^2$, Z$^2$, R$^1$, R$^2$, R$^3$, R$^4$, R$^5$, R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$ and R$^{28}$ is a constituent including Bm or Dm, and at least one of Bm and Dm is a photosensitizer for phototherapy. For example, in one preferred embodiment, at least one of Y$^2$, R$^1$, R$^2$, R$^3$, R$^4$, R$^5$, R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$ and R$^{28}$ is a constituent including Bm, and Z$^2$ is a constituent including Dm. In such a preferred embodiment, one of Bm and Dm is a peptide, and the other of Bm and Dm is a photosensitizer for phototherapy.

In still another family of preferred embodiments of the indocyanine dyes of Formula 2, at least one of Y$^2$, Z$^2$, R$^1$, R$^2$, R$^3$, R$^4$, R$^5$, R$^{16}$, R$^{17}$, R$^{18}$, R$^{19}$, R$^{20}$, R$^{21}$, R$^{22}$, R$^{23}$, R$^{24}$, R$^{25}$, $R^{26}$, $R^{27}$ and $R^{28}$ is a constituent including Bm or Dm. However, in this preferred family, Bm and/or Dm is selected from the group consisting of a protein, a cell, a metal chelating agent, a radioactive or nonradioactive metal complex, a photosensitizer for phototherapy, and an echogenic agent.

A third aspect of the invention is preferably directed to cyanine dyes of Formula 3, wherein $W^3$ and $X^3$ may be the same or different and are selected from the group consisting of —C(CH$_3$)$_2$, —C((CH$_2$)$_a$OH)CH$_3$, —C((CH$_2$)$_a$OH)$_2$, —C((CH$_2$)$_a$CO$_2$H)CH$_3$, —C((CH$_2$)$_a$CO$_2$H)$_2$, —C((CH$_2$)$_a$NH$_2$)CH$_3$, —C((CH$_2$)$_a$NH$_2$)$_2$, C((CH$_2$)$_a$NR$^3$R$^4$)$_2$, —NR$^3$, and —S—; $Y^3$ is selected from the group consisting of hydrogen, C$_1$-C$_{10}$ alkyl, C$_5$-C$_{20}$ aryl, C$_1$-C$_{10}$ alkoxyl, C$_1$-C$_{10}$ polyalkoxyalkyl, C$_1$-C$_{20}$ polyhydroxyalkyl, C$_5$-C$_{20}$ polyhydroxyaryl, C$_1$-C$_{10}$ aminoalkyl, —CH$_2$(CH$_2$OCH$_2$)$_b$—CH$_2$—OH, —(CH$_2$)$_a$—CO$_2$H, —(CH$_2$)$_a$—CONH-Bm, —CH$_2$—(CH$_2$OCH$_2$)$_b$—CH$_2$—CONH-Bm, —(CH$_2$)$_a$—NHCO-Bm, —CH$_2$—(CH$_2$OCH$_2$)$_b$—CH$_2$—NHCO-Bm, —(CH$_2$)$_a$—NR$^3$R$^4$, and —CH$_2$(CH$_2$OCH$_2$)$_b$—CH$_2$NR$^3$R$^4$; $Z^3$ is selected from the group consisting of hydrogen, C$_1$-C$_{10}$ alkyl, C$_5$-C$_{20}$ aryl, C$_1$-C$_{10}$ alkoxyl, C$_1$-C$_{10}$ polyalkoxyalkyl, C$_1$-C$_{20}$ polyhydroxyalkyl, C$_5$-C$_{20}$ polyhydroxyaryl, C$_1$-C$_{10}$ aminoalkyl, —CH$_2$(CH$_2$OCH$_2$)$_b$—CH$_2$—OH, —(CH$_2$)$_a$—CO$_2$H, —(CH$_2$)$_a$—CONH-Dm, —CH$_2$—(CH$_2$OCH$_2$)$_b$—CH$_2$—CONH-Dm, —(CH$_2$)$_a$—NHCO-Dm, —CH$_2$—(CH$_2$OCH$_2$)$_b$—CH$_2$—NHCO-Dm, —(CH$_2$)$_a$—NR$^3$R$^4$, and —CH$_2$(CH$_2$OCH$_2$)$_b$—CH$_2$NR$^3$R$^4$; $A_1$ is a single or a double bond; $B_1$, $C_1$, and $D_1$ are independently selected from the group consisting of —O—, —S—, NR$^3$, (CH$_2$)$_a$—CR$^1$R$^2$, and —CR$^1$; $A_1$, $B_1$, $C_1$, and $D_1$ may together form a 6- to 10-membered carbocyclic ring or a 6- to 10-membered heterocyclic ring optionally containing one or more oxygen, nitrogen, or sulfur atom; $a_3$ and $b_3$ are independently from 0 to 3; $R^1$ to $R^4$, and $R^{29}$ to $R^{37}$ are independently selected from the group consisting of hydrogen, C$_1$-C$_{10}$ alkyl, C$_5$-C$_{12}$ aryl, C$_1$-C$_{10}$ alkoxyl, C$_1$-C$_{10}$ polyhydroxyalkyl, C$_5$-C$_{12}$ polyhydroxyaryl, C$_1$-C$_{10}$ aminoalkyl, mono- or oligosaccharide, peptide with 2 to 30 amino acid units, —CH$_2$(CH$_2$OCH$_2$)$_b$—CH$_2$—OH, —(CH$_2$)$_a$—CO$_2$H, —(CH$_2$)$_a$—CONH-Bm, —CH$_2$—(CH$_2$OCH$_2$)$_b$—CH$_2$—CONH-Bm, —(CH$_2$)$_a$—NHCO-Bm, —CH$_2$—(CH$_2$OCH$_2$)$_b$—CH$_2$—NHCO-Bm, —(CH$_2$)$_a$—OH and —CH$_2$—(CH$_2$OCH$_2$)$_b$—CO$_2$H; Bm and Dm are independently selected from the group consisting of peptide containing 2 to 30 amino acid units, an antibody, a mono- or oligosaccharide, a glycopeptide, a metal chelating agent, a radioactive or nonradioactive metal complex, and an echogenic agent; a and c are independently from 1 to 10; and b and d are independently from 1 to 30.

Yet a fourth aspect of the invention is preferably directed to indocyanine dyes having the general Formula 4, wherein $W^4$ and $X^4$ may be the same or different and are selected-from the group consisting of —C(CH$_3$)$_2$, —C((CH$_2$)$_a$OH)CH$_3$, —C((CH$_2$)$_a$OH)$_2$, —C((CH$_2$)$_a$CO$_2$H)CH$_3$, —C((CH$_2$)$_a$CO$_2$H)$_2$, —C((CH$_2$)$_a$NH$_2$)CH$_3$, C((CH$_2$)$_a$NH$_2$)$_2$, —C((CH$_2$)$_a$NR$^3$R$^4$)$_2$, —NR$^3$, and —S—; $Y^4$ is selected from the group consisting of hydrogen, C$_1$-C$_{10}$ alkyl, C$_5$-C$_{20}$ aryl, C$_1$-C$_{10}$ alkoxyl, C$_1$-C$_{10}$ polyalkoxyalkyl, C$_1$-C$_{20}$ polyhydroxyalkyl, C$_5$-C$_{20}$ polyhydroxyaryl, C$_1$-C$_{10}$ aminoalkyl, —CH$_2$(CH$_2$OCH$_2$)$_b$—CH$_2$—OH, —(CH$_2$)$_a$—CO$_2$H, —(CH$_2$)$_a$—CONH-Bm, —CH$_2$—(CH$_2$OCH$_2$)$_b$—CH$_2$—CONH-Bm, —(CH$_2$)$_a$—NHCO-Bm, —CH$_2$—(CH$_2$OCH$_2$)$_b$—CH$_2$—NHCO-Bm, —(CH$_2$)$_a$—NR$^3$R$^4$, and —CH$_2$(CH$_2$OCH$_2$)$_b$—CH$_2$NR$^3$R$^4$; $Z^4$ is selected from the group consisting of hydrogen, C$_1$-C$_{10}$ alkyl, C$_5$-C$_{20}$ aryl, C$_1$-C$_{10}$ alkoxyl, C$_1$-C$_{10}$ polyalkoxyalkyl, C$_1$-C$_{20}$ polyhydroxyalkyl, C$_5$-C$_{20}$ polyhydroxyaryl, C$_1$-C$_{10}$ aminoalkyl, —CH$_2$(CH$_2$OCH$_2$)$_b$—CH$_2$—OH, —(CH$_2$)$_a$—CO$_2$H, —(CH$_2$)$_a$—CONH-Dm, —CH$_2$—(CH$_2$OCH$_2$)$_b$—CH$_2$—CONH-Dm, —(CH$_2$)$_a$—NHCO-Dm, —CH$_2$—(CH$_2$OCH$_2$)$_b$—CH$_2$—NHCO-Dm, —(CH$_2$)$_a$—NR$^3$R$^4$, and —CH$_2$(CH$_2$OCH$_2$)$_b$—CH$_2$NR$^3$R$^4$; $A_2$ is a single or a double bond; $B_2$, $C_2$, and $D_2$ are independently selected from the group consisting of —O—, —S—, NR$^3$, (CH2)$_a$—CR$^1$R$^2$, and —CR$^1$; $A_2$, $B_2$, $C_2$, and $D_2$ may together form a 6- to 10-membered carbocyclic ring or a 6- to 10-membered heterocyclic ring optionally containing one or more oxygen, nitrogen, or sulfur atom; $a_4$ and $b_4$ are independently from 0 to 3; $R^1$ to $R^4$, and $R^{45}$ to $R^{57}$ are independently selected from the group consisting of hydrogen, C$_1$-C$_{10}$ alkyl, C$_5$-C$_{12}$ aryl, C$_1$-C$_{10}$ alkoxyl, C$_1$-C$_{10}$ polyhydroxyalkyl, C$_5$-C$_{12}$ polyhydroxyaryl, C$_1$-C$_{10}$ aminoalkyl, mono- or oligosaccharide, peptide with 2 to 30 amino acid units, —CH$_2$(CH$_2$OCH$_2$)$_b$—CH$_2$—OH, —(CH$_2$)$_a$—CO$_2$H, —(CH$_2$)$_a$—CONH-Bm, —CH$_2$—(CH$_2$OCH$_2$)$_b$—CH$_2$—CONH-Bm, —(CH$_2$)$_a$—NHCO-Bm, —CH$_2$—(CH$_2$OCH$_2$)$_b$—CH$_2$—NHCO-Bm, —(CH$_2$)$_a$—OH and —CH$_2$—(CH$_2$OCH$_2$)$_b$—CO$_2$H; Bm and Dm are independently selected from the group consisting of a peptide containing 2 to 30 amino acid units, an antibody, a mono- or oligosaccharide, a glycopeptide, a metal chelating agent, a radioactive or nonradioactive metal complex, and an echogenic agent; a and c are independently from 1 to 10; and b and d independently from 1 to 30.

Still a fifth aspect of the invention includes cyanine dyes preferably having the general Formula 5, wherein $W^5$ and $X^5$ may be the same or different and are selected from the group consisting of —C(CH$_3$)$_2$, —C((CH$_2$)$_a$OH)CH$_3$, —C((CH$_2$)$_a$OH)$_2$, —C((CH$_2$)$_a$CO$_2$H)CH$_3$, C((CH$_2$)$_a$CO$_2$H)$_2$, —C((CH$_2$)$_a$NH$_2$)CH$_3$, —C((CH$_2$)$_a$NH$_2$)$_2$, —C((CH$_2$)$_a$NR$^3$R$^4$)$_2$, —NR$^3$, and —S—; $Y^5$ is selected from the group consisting of hydrogen, C$_1$-C$_{10}$ alkyl, C$_5$-C$_{20}$ aryl, C$_1$-C$_{10}$ alkoxyl, C$_1$-C$_{10}$ polyalkoxyalkyl, C$_1$-C$_{20}$ polyhydroxyalkyl, C$_5$-C$_{20}$ polyhydroxyaryl, C$_1$-C$_{10}$ aminoalkyl, —CH$_2$(CH$_2$OCH$_2$)$_b$—CH$_2$—OH, —(CH$_2$)$_a$—CO$_2$H, —(CH$_2$)$_a$—CONH-Bm, —CH$_2$—(CH$_2$OCH$_2$)$_b$—CH$_2$—CONH-Bm, —(CH$_2$)$_a$—NHCO-Bm, —CH$_2$—(CH$_2$OCH$_2$)$_b$—CH—NHCO-Bm, —(CH$_2$)$_a$—NR$^3$R$^4$, and —CH$_2$(CH$_2$OCH$_2$)$_b$—CH$_2$NR$^3$R$^4$; $Z^5$ is selected from the group consisting of hydrogen, C$_1$-C$_{10}$ alkyl, C$_5$-C$_{20}$ aryl, C$_1$-C$_{10}$ alkoxyl, C$_1$-C$_{10}$ polyalkoxyalkyl, C$_1$-C$_{20}$ polyhydroxyalkyl, C$_5$-C$_{20}$ polyhydroxyaryl, C$_1$-C$_{10}$ aminoalkyl, —CH$_2$(CH$_2$OCH$_2$)$_b$—CH$_2$—OH , —(CH$_2$)$_a$—CO$_2$H, —(CH$_2$)$_a$—CONH-Dm, —CH$_2$—(CH$_2$OCH$_2$)$_b$—CH$_2$—CONH-Dm, —(CH$_2$)$_a$—NHCO-Dm, —CH$_2$—(CH$_2$OCH$_2$)$_b$—CH$_2$—NHCO-Dm, —(CH$_2$)$_a$—NR$^3$R$^4$, and —CH$_2$(CH$_2$OCH$_2$)$_b$—H$_2$NR$^3$R$^4$; $A_3$ is a single or a double bond; $B_3$, $C_3$, and $D_3$ are independently selected from the group consisting of —O—, —S—, NR$^3$, (CH$_2$)$_a$—CR$^1$R$^2$, and —CR$^1$; $A_3$, $B_3$, $C_3$, and $D_3$ may together form a 6- to 10-membered carbocyclic ring or a 6- to 10-membered heterocyclic ring optionally containing one or more oxygen, nitrogen, or sulfur atom; $a_5$ is from 0 to 3; $R^1$ to $R^4$, and $R^{58}$ to $R^{66}$ are independently selected from the group consisting of hydrogen, C$_1$-C$_{10}$ alkyl, C$_5$-C$_{12}$ aryl, C$_1$-C$_{10}$ alkoxyl, C$_1$-C$_{10}$ polyhydroxyalkyl, C$_5$-C$_{12}$ polyhydroxy aryl, C$_1$-C$_{10}$ aminoalkyl, mono- or oligosaccharide, peptide with 2 to 30 amino acid units, —CH$_2$(CH$_2$OCH$_2$)$_b$—CH$_2$—OH, —(CH$_2$)$_a$—CO$_2$H, —(CH$_2$)$_a$—CONH-Bm, —CH$_2$—(CH$_2$OCH$_2$)$_b$—CH$_2$—CONH-Bm, —(CH$_2$)$_a$—NHCO-Bm, —CH$_2$—(CH$_2$OCH$_2$)$_b$—CH$_2$—NHCO-Bm, —(CH$_2$)$_a$—OH and —CH$_2$—(CH$_2$OCH$_2$)$_b$—CO$_2$H; Bm and Dm are independently selected from the group consisting of a peptide containing 2 to 30 amino acid units, an antibody, a mono- or oligosaccharide, a glycopeptide, a metal chelating agent, a radioactive or nonradioactive metal complex, and an echogenic agent; a and c are independently from 1 to 10; and b and d are independently from 1 to 30.

Still a sixth aspect of the invention is directed to indocyanine dyes preferably having the general Formula 6, wherein $W^6$ and $X^6$ may be the same or different and are selected from the group consisting of —C(CH$_3$)$_2$, —C((CH$_2$)$_a$OH)CH$_3$, —C((CH$_2$)$_a$OH)$_2$, —C((CH$_2$)$_a$CO$_2$H)CH$_3$, —C((CH$_2$)$_a$CO$_2$H)$_2$, —C((CH$_2$)$_a$NH$_2$)CH$_3$, C((CH$_2$)$_a$NH$_2$)$_2$, C((CH$_2$)$_a$NR$^3$R$^4$)$_2$, —NR$^3$, and —S—; $Y^6$ is selected from the group consisting of hydrogen, $C_1$-$C_{10}$ alkyl, $C_5$-$C_{20}$ aryl, $C_1$-$C_{10}$ alkoxyl, $C_1$-$C_{10}$ polyalkoxyalkyl, $C_1$-$C_{20}$ polyhydroxyalkyl, $C_5$-$C_{20}$ polyhydroxyaryl, $C_1$-$C_{10}$ aminoalkyl, —CH$_2$(CH$_2$OCH$_2$)$_b$—CH$_2$—OH, —(CH$_2$)$_a$—CO$_2$H, —(CH$_2$)$_a$—CONH-Bm, —CH$_2$—(CH$_2$OCH$_2$)$_b$—CH$_2$—CONH-Bm, —(CH$_2$)$_a$—NHCO-Bm, —CH$_2$—(CH$_2$OCH$_2$)$_b$—CH$_2$—NHCO-Bm, —(CH$_2$)$_a$—NR$^3$R$^4$, and —CH$_2$(CH$_2$OCH$_2$)$_b$—CH$_2$NR$^3$R$^4$; $Z^6$ is selected from the group consisting of hydrogen, $C_1$-$C_{10}$ alkyl, $C_5$-$C_{20}$ aryl, $C_1$-$C_{10}$ alkoxyl, $C_{-C10}$ polyalkoxyalkyl, $C_1$-$C_{20}$ polyhydroxyalkyl, $C_5$-$C_{20}$ polyhydroxyaryl, $C_1$-$C_{10}$ aminoalkyl, —CH$_2$(CH$_2$OCH$_2$)$_b$—CH$_2$—OH, —(CH$_2$)$_a$—CO$_2$H, —(CH$_2$)$_a$—CONH-Dm, —CH$_2$—(CH$_2$OCH$_2$)$_b$—CH$_2$—CONH-Dm, —(CH$_2$)$_a$—NHCO-Dm, —CH$_2$—(CH$_2$OCH$_2$)$_b$—CH$_2$—NHCO-Dm, —(CH$_2$)$_a$—NR$^3$R$^4$, and —CH$_2$(CH$_2$OCH$_2$)$_b$—CH$_2$NR$^3$R$^4$; A4 is a single or a double bond; B$_4$, C$_4$, and D$_4$ are independently selected from the group consisting of —O—, —S—, NR$^3$, (CH$_2$)$_a$—CR$^1$R$^2$, and —CR$^1$; A4, B$_4$, C$_4$, and D$_4$ may together form a 6- to 10-membered carbocyclic ring or a 6- to 10-membered heterocyclic ring optionally containing one or more oxygen, nitrogen, or sulfur atom; $a_6$ is from 0 to 3; $R^1$ to $R^4$, and $R^{67}$ to $R^{79}$ are independently selected from the group consisting of hydrogen, $C_1$-$C_{10}$ alkyl, $C_5$-$C_{12}$ aryl, $C_1$-$C_{10}$ alkoxyl, $C_1$-$C_{10}$ polyhydroxyalkyl, $C_5$-$C_{12}$ polyhydroxyaryl, $C_1$-$C_{10}$ aminoalkyl, mono- or oligosaccharide, peptide with 2 to 30 amino acid units, —CH$_2$(CH$_2$OCH$_2$)$_b$—CH$_2$—OH, —(CH$_2$)$_a$—CO$_2$H, —(CH$_2$)$_a$—CONH-Bm, —CH$_2$—(CH$_2$OCH$_2$)$_b$—CH$_2$—CONH-Bm, —(CH$_2$)$_a$—NHCO-Bm, —CH$_2$—(CH$_2$OCH$_2$)$_b$—CH$_2$—NHCO-Bm, —(CH$_2$)$_a$—OH and —CH$_2$—(CH$_2$OCH$_2$)$_b$—CO$_2$H; Bm and Dm are independently selected from the group consisting of a peptide containing 2 to 30 amino acid units, an antibody, a mono- or oligosaccharide, a glycopeptide, a metal chelating agent, a radioactive or nonradioactive metal complex, and an echogenic agent; a and c are independently from 1 to 10; and b and d are independently from 1 to 30.

This invention is also related to the method of conjugating the inventive dyes to peptides or biomolecules by solid phase or solution synthesis methods. Accordingly, the term "dye" or the like herein shall refer to the compounds representatively illustrated in Formulas 1-6, including described bioconjugates of such compounds. For example, in some preferred bioconjugates of the invention, one or more of the constituents represented by Y groups, Z groups, and R groups of Formulas 1-6 is a constituent including Bm or Dm, wherein Bm and Dm may each be any of a peptide, a protein, a cell, a metal chelating agent, a radioactive or nonradioactive metal complex, a photosensitizer for phototherapy, and an echogenic agent. In one preferred family of embodiments of Formulas 1-6, one or more of the constituents represented by Y groups, Z groups, and R groups is a constituent including Bm or Dm, and at least one of Bm and Dm is a peptide such as Octreotide, Octreotate, Bombesin, Cholecystokinin, or Neurotensin. In another preferred family of embodiments of Formulas 1-6, one or more of the constituents represented by Y groups, Z groups, and R groups is a constituent including Bm or Dm, and at least one of Bm and Dm is a photosensitizer for phototherapy. For example, one preferred dye of one of Formulas 1-6 has two Y, Z, and/or R group constituents of which a Bm is a part. In this preferred dye, one Bm is a photosensitizer, and the other Bm is a peptide. In still another preferred family of embodiments of Formulas 1-6, one or more of the constituents represented by Y groups, Z groups, and R groups is a constituent including Bm or Dm, and Bm and/or Dm is selected from the group consisting of a protein, a cell, a metal chelating agent, a radioactive or nonradioactive metal complex, a photosensitizer for phototherapy, and an echogenic agent.

Figure 6:
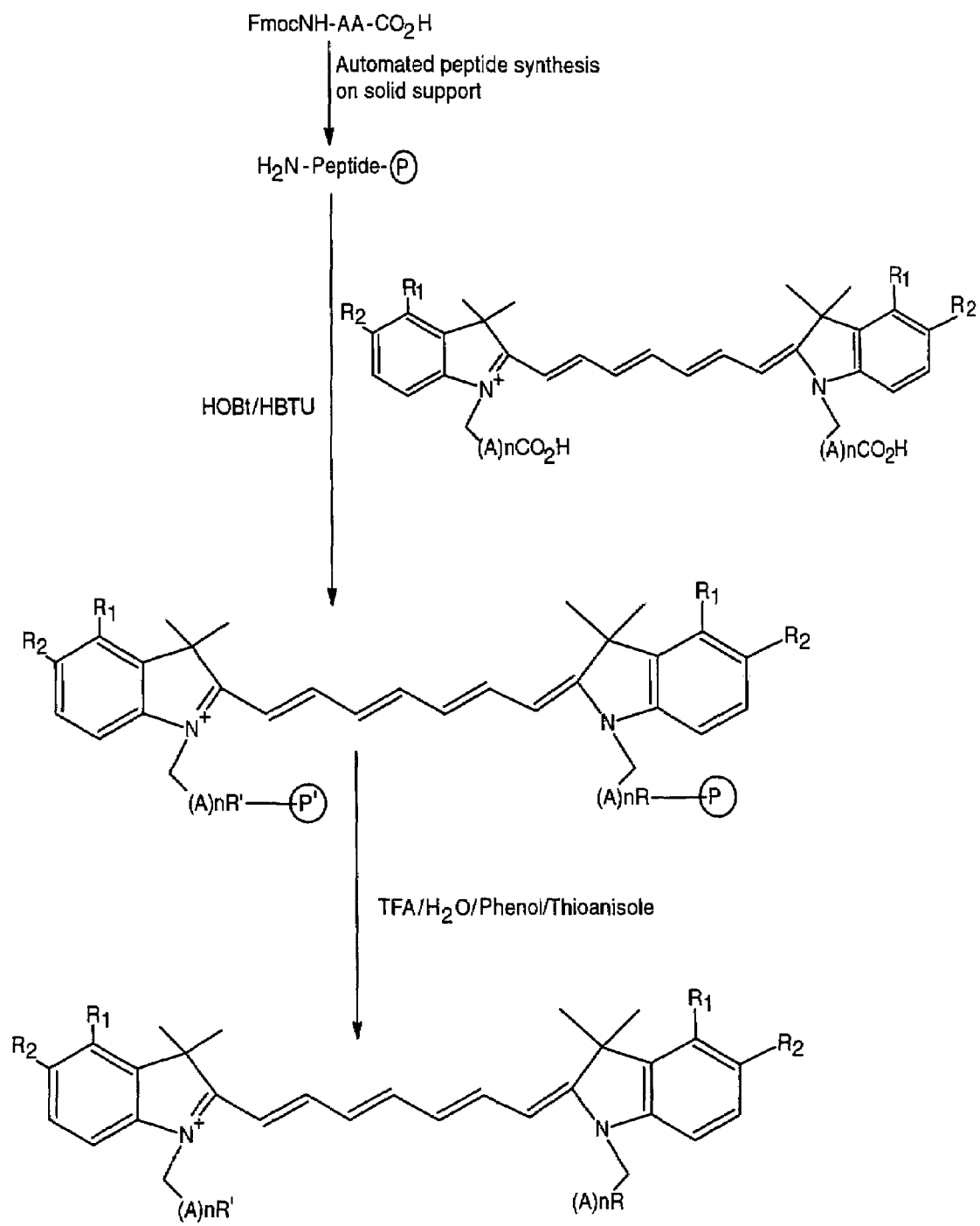
FIG. 6 shows the reaction pathway for the synthesis of cyanine dye bioconjugates.

FIG. 6 illustrates the synthetic scheme for bioconjugates incorporating the cyanine dyes of FIGS. 1-5, using automated peptide synthesis in a solid support, where A=CH$_2$ or CH$_2$OCH$_2$; $R_1$=$R_2$=H (Formula 1) or $R_1$, $R_2$=fused phenyl (Formula 2); AA=amino acids; R=CONH peptide; R'=R (bis conjugate) or COOH (mono conjugate);

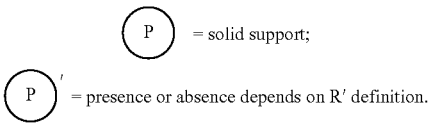

This invention is also related to the method of preventing fluorescence quenching. It is known that cyanine dyes generally form aggregates in aqueous media, leading to fluorescence quenching. Where the presence of a hydrophobic core in the dyes leads to fluorescence quenching, the addition of a biocompatible organic solvent, such as 1-50% dimethylsulfoxide (DMSO) for example, restored fluorescence by preventing aggregation and allowed in vivo organ visualization. Large fluorescence enhancement of dyes have been observed under the condition where the dye is encapsulated in, i.e. forms an inclusion complex with, cyclodextrins (W. R. Bergmark et al., Dramatic fluorescence effects for coumarin laser dyes coincluded with organic solvents in cyclodextrins. *J. Phys. Chem.*, 1990, 94, 50208-5022). However, in vivo fluorescence enhancement of dyes coinjected with biocompatible organic solvents has not been previously described. Suitable organic solvent include, but are not limited to dimethylsulfoxide (DMSO), ethyl alcohol, isopropyl alcohol, glycerol, and other biocompatible polyols such as sorbitol, mannitol, xylitol, lactitol, erythritol, polydextrose, sucrose, fructose, maltose, hydrogenated starch hydrolysate (HSH), isomalt (palitinit), polyglycerol, hyperbranched polyglycerol, acetylated polyols, maltodextrine, cyclodextrine, dianhydosorbitol, starches, polysaccharides, etc. as known to one skilled in the art.

The dye-biomolecule conjugates are used for optical tomographic, endoscopic, photoacoustic, phototherapeutic, and sonofluorescent applications for the detection and treatment of tumors and other abnormalities. The phototherapeutic photosensitizers may include those operating via direct (Type 1) mechanism as described by Rajagopalan et al. (U.S. Pat. No. 6,485,704, and U.S. patent application Ser. Nos. 09/766,347, and 09/898,887, incorporated herein by reference in their entirety), or by photodynamic (PDT or Type II) mechanism as described by Jori et al. (Tumour photosensitizers: approaches to enhance the selectivity and efficiency of photodynamic therapy, Journal of Photochemistry and Photobiology B: Biology 36 (1996) 87-93; Novel Therapeutic Modalities Based on Photosensitized Processes, EPA Newsletter No. 60, (July 1997) 12-18; Far-red-absorbing photosensitizers: their use in the photodynamic therapy of tumours, J. Photochem. Photobiol. A: Chem., 62 (1992) 371-378; and Second Generation Photosensitizers for the Photodynamic Therapy of Tumours, Light in Biology and Medicine, Vol. 2, (1991) 253-266), incorporated herein by reference in their entirety. Type 1 photosensitizers are those moieties that produce reactive intermediates such as free radicals, nitrenes, carbenes, and the like upon photoactivation. These include azides, peroxides, disulfides, sulfenates, and the like. Type II sensitizers are those that produce singlet oxygen species upon photoactivation. These include phthalocyanines, porphyrins, and the like. Incidentally, U.S. Pat. No. 6,217,848 is also herein incorporated by reference in its entirety.

The bioconjugates of the present invention are prepared by the standard bioconjugate chemistry methods known in the art as illustrated in the forthcoming examples. Typically, the coupling between the dyes and the photosensitizers of the present invention is achieved by reacting the carboxyl group in one of the two aforementioned components with the aminogroup of the other component that results in the formation of the amide bond between the two units. Alternatively, if the two components contain either an amino or a hydroxyl group, the coupling would result in the formation of ester, urea, thiourea, carbamate, or carbonate species. Indeed, in one preferred family of embodiments, the compounds of formulas 1-4 have at least one constituent that includes at least one of Bm and Dm. In one preferred subfamily of such embodiments, at least one of Bm and Dm is a photosensitizer that may be utilized in phototherapy.

The inventive composition may be administered for imaging by more than one modality. As one example, a paramagnetic metal ion such as gadolinium or manganese may be included in the chemical formula and the composition may be imaged by optical imaging alone, by magnetic resonance imaging (MR) alone, or by both optical and MR modalities. As another example, the composition may be imaged by optical imaging alone, by nuclear imaging alone, or by both optical and nuclear imaging modalities when a radioactive isotope is included in the chemical formula, such as replacing a halogen atom with a radioactive halogen, and/or including a radioactive metal ion such as $Tc^{99}$, $In^{111}$, etc.

It will also be appreciated that the inventive compositions may be administered with other contrast agents or media used to enhance an image from a non-optical modality. These include agents for enhancing an image obtained by modalities including but not limited to MR, ultrasound (US), x-ray, positron emission tomography (PET), computed tomography (CT), single photon emission computed tomography (SPECT), etc. Both optical and non-optical agents may be formulated as a single composition (that is, one composition containing one, two or more components, for example, an optical agent and a MR agent), or may be formulated as separate compositions. The inventive optical imaging contrast agent and the non-optical contrast agent are administered in doses effective to achieve the desired enhancement, diagnosis, therapy, etc., as known to one skilled in the art. The inventive compositions, either alone or combined with a contrast agent, may be administered to a patient, typically a warm-blooded animal, systemically or locally to the organ or tissue to be imaged. The patient is then imaged by optical imaging and/or by another modality. As one example of this embodiment, the inventive compounds may be added to contrast media compositions. As another example, the inventive compositions may be co-administered with contrast media, either simultaneously or within the same diagnostic and/or therapeutic procedure (for example, administering the inventive composition and administering a contrast agent then performing optical imaging followed by another imaging modality, or administering the inventive composition and administering a contrast agent then performing another imaging modality followed by optical imaging, or administering the inventive composition and optical imaging, then administering a contrast agent and MR, US, CT, etc. imaging, or administering a contrast agent and imaging by MR, US, CT, etc., then administering the inventive composition and optical imaging, or administering the inventive composition and a contrast agent, and simultaneously imaging by an optical modality and MR, US, CT, etc.). As another example, an optical imaging agent may be added as an additive or excipient for a non-optical imaging modality. In this embodiment, the optically active component, such as the dyes disclosed herein, could be added as a buffering agent to control pH or as a chelating agent to improve formulation stability, etc. in CT contrast media, MR contrast media, x-ray contrast media, US contrast media, etc. The CT, MR, x-ray, US contrast media would then also function as an optical imaging agent. The information obtained from the modality using the non-optical contrast agent is useful in combination with the image obtained using the optical contrast agent.

Dye-biomolecule conjugates of the invention are also used for localized therapy. This may be accomplished by attaching a porphyrin or photodynamic therapy agent to a bioconjugate, shining light of appropriate wavelength for detection and treatment of the abnormality.

The inventive conjugates can also be used for the detection of the presence of tumors and other abnormalities by monitoring the blood clearance profile of the conjugates, for laser assisted guided surgery for the detection of small micrometastases of, e.g., somatostatin subtype 2 (SST-2) positive tumors, upon laparoscopy, and for diagnosis of atherosclerotic plaques and blood clots.

The compositions of the invention can be formulated into diagnostic and therapeutic compositions for enteral or parenteral administration. These compositions contain an effective amount of the dye along with conventional pharmaceutical carriers and excipients appropriate for the type of administration contemplated. For example, parenteral formulations advantageously contain the inventive agent in a sterile aqueous solution or suspension. Parenteral compositions may be injected directly or mixed with a large volume parenteral composition for systemic administration. Such solutions also may contain pharmaceutically acceptable buffers and, optionally, electrolytes such as sodium chloride.

Formulations for enteral administration may vary widely, as is well known in the art. In general, such formulations are liquids, which include an effective amount of the inventive agent in aqueous solution or suspension. Such enteral compositions may optionally include buffers, surfactants, thixotropic agents, and the like. Compositions for oral administration may also contain flavoring agents and other ingredients for enhancing their organoleptic qualities.

In one embodiment, the agents may be formulated as micelles, liposomes, microcapsules, or other microparticles. These formulations may enhance delivery, localization, target specificity, administration, etc. of the agents. Preparation and loading of these are well known in the art.

As one example, liposomes may be prepared from dipalmitoyl phosphatidylcholine (DPPC) or egg phosphatidylcholine (PC) because this lipid has a low heat transition. Liposomes are made using standard procedures as known to one skilled in the art (e.g., Braun-Falco et al., (Eds.), Griesbach Conference, *Liposome Dermatics,* Springer-Verlag, Berlin (1992), pp. 69-81; 91-117 which is expressly incorporated by reference herein). Polycaprolactone, poly(glycolic)acid, poly(lactic)acid, polyanhydride or lipids may be formulated as microspheres. As an illustrative example, the optical agent may be mixed with polyvinyl alcohol (PVA), the mixture then dried and coated with ethylene vinyl acetate, then cooled again with PVA. In a liposome, the optical agent may be within one or both lipid bilayers, in the aqueous between the bilayers, or with the center or core. Liposomes may be modified with other molecules and lipids to form a cationic liposome. Liposomes may also be modified with lipids to render their surface more hydrophilic which increases their circulation time in the bloodstream. The thus-modified liposome has been termed a "stealth" liposome, or a long-lived liposome, as described in U.S. Pat. No. 6,258,378, and in Stealth Liposomes, Lasic and Martin (Eds.) 1995 CRC Press, London, which are expressly incorporated by reference herein. Encapsulation methods include detergent dialysis, freeze drying, film forming, injection, as known to one skilled in the art and disclosed in, for example, U.S. Pat. No. 6,406,713 which is expressly incorporated by reference herein in its entirety.

The agent formulated in liposomes, microcapsules, etc. may be administered by any of the routes previously described. In a formulation applied topically, the optical agent is slowly released over time. In an injectable formulation, the liposome, capsule, etc., circulates in the bloodstream and is delivered to the desired site.

The diagnostic compositions are administered in doses effective to achieve the desired enhancement. Such doses may vary widely, depending upon the particular dye employed, the organs or tissues to be imaged, the imaging equipment being used, and the like. The diagnostic compositions of the invention are used in the conventional manner. The compositions may be administered to a patient, typically a warm-blooded animal, either systemically or locally to the organ or tissue to be imaged, and the patient then subjected to the imaging procedure.

The inventive compositions and methods represent an important approach to the synthesis and use of novel cyanine and indocyanine dyes with a variety of photophysical and chemical properties. The combination also represents an important approach to the use of small molecular targeting groups to image tumors by optical methods. The invention is further detailed in the following Examples, which are offered by way of illustration and are not intended to limit the scope of the invention in any manner.

EXAMPLE 1

Synthesis of Bis(ethylcarboxymethyl)indocyanine Dye (FIG. 1, $R_1$, $R_2$=fused phenyl; A=$CH_2$, n=1 and R=R'=$CO_2H$)

A mixture of 1,1,2-trimethyl-[1H]-benz[e]indole (9.1 g, 43.58 mmoles) and 3-bromopropanoic acid (10.0 g, 65.37 mmoles) in 1,2-dichlorobenzene (40 mL) was heated at 110° C. for 12 hours. The solution was cooled to room temperature and the red residue obtained was filtered and washed with acetonitrile:diethyl ether (1:1) mixture. The solid obtained was dried under vacuum to give 10 g (64%) of light brown powder. A portion of this solid (6.0 g; 16.56 mmoles), glutaconaldehyde dianil monohydrochloride (2.36 g, 8.28 mmoles) and sodium acetate trihydrate (2.93 g, 21.53 mmoles) in ethanol (150 mL) were refluxed for 90 minutes. After evaporating the solvent, 40 mL of a 2 N aqueous HCl was added to the residue. The mixture was centrifuged and the supernatant was decanted. This procedure was repeated until the supernatant became nearly colorless. About 5 mL of water:acetonitrile (3:2) mixture was added to the solid residue and lyophilized to obtain 2 g of dark green flakes. The purity of the compound was established with $^1$H-NMR and liquid chromatography-mass spectroscopy (LC-MS).

EXAMPLE 2

Synthesis of Bis(pentylcarboxymethyl)indocyanine Dye (FIG. 1, $R_1$, $R_2$=fused Phenyl; A=$CH_2$, n=4 and R=R'=$CO_2H$)

A mixture of 1,1,2-trimethyl-[1H]-benz[e]indole (20 g, 95.6 mmoles) and 6-bromohexanoic acid (28.1 g, 144.1 mmoles) in 1,2-dichlorobenzene (250 mL) was heated at 110° C. for 12 hours. The green solution was cooled to room temperature and the brown solid precipitate formed was collected by filtration. After washing the solid with 1,2-dichlorobenzene and diethyl ether, the brown powder obtained (24 g, 64%) was dried under vacuum at room temperature. A portion of this solid (4.0 g; 9.8 mmoles), glutaconaldehyde dianil monohydrochloride (1.4 g, 5 mmoles) and sodium acetate trihydrate (1.8 g, 12.9 mmoles) in ethanol (80 mL) were refluxed for 1 hour. After evaporating the solvent, 20 mL of a 2 N aqueous HCl was added to the residue. The mixture was centrifuged and the supernatant was decanted. This procedure was repeated until the supernatant became nearly colorless. About 5 mL of water:acetonitrile (3:2) mixture was added to the solid residue and lyophilized to obtain about 2 g of dark green flakes. The purity of the compound was established with $^1$H-NMR and LC-MS.

EXAMPLE 3

Synthesis of Bisethylcarboxymethylindocyanine Dye (FIG. 1, $R_1$=$R_2$=H; A=$CH_2$, n=1 and R=R'=$CO_2H$)

This compound was prepared as described in Example 1 except that 1,1,2-trimethylindole was used as the starting material.

EXAMPLE 4

Synthesis of Bis(hexaethyleneglycolcarboxymethyl)indocyanine Dye (FIG. 1, $R_1$=$R_2$=fused phenyl; A=$CH_2OCH_2$, n=6 and R=R'=$CO_2H$)

This compound was prepared as described in Example 1 except that ☐-bromohexaoxyethyleneglycolpropiolic acid was used in place of bromopropanoic acid and the reaction was carried out in 1,2-dimethoxypropane.

EXAMPLE 5

Synthesis of Bisethylcarboxymethylindocyanine Dye (FIG. 2, $R_1$=$R_2$=fused phenyl; A=$CH_2$, and n=0)

A solution of 50 ml of dimethylformamide and benzyl bromoacetate (16.0 g, 70 mmol) was stirred in a 100-mL three-neck flask. Solid potassium bicarbonate (7.8 g, 78 mmol) was added. The flask was purged with argon and cooled to 0° C. with an ice bath. To the stirring mixture was added dropwise a solution of ethanolamine (1.9 g, 31 mmol) and 4 ml of dimethylformamide over 5 minutes. After the addition was complete the mixture was stirred for 1 hour at 0° C. The ice bath was removed and the mixture stirred at room temperature overnight. The reaction mixture was partitioned between 100 ml of methylene chloride and 100 ml of saturated sodium bicarbonate solution. The layers were separated and the methylene chloride layer was again washed with 100 ml of saturated sodium bicarbonate solution. The combined aqueous layers were extracted twice with 25 ml of methylene chloride. The combined methylene chloride layers were washed with 100 ml of brine, and dried over magnesium sulfate. The methylene chloride was removed with aspirator vacuum at about 35° C., and the remaining dimethylformamide was removed with vacuum at about 45° C. The crude material was left on a vacuum line overnight at room temperature.

The crude material was then dissolved in 100 ml of methylene chloride at room temperature. Triphenylphosphine (8.91 g, 34 mmol) was added and dissolved with stirring. An argon purge was started and the mixture was cooled to 0° C. with an ice bath. The N-bromosuccinimide (6.05 g, 34 mmol) was added portionwise over two minutes. The mixture was stirred for 1.5 hours at 0° C. The methylene chloride was removed with vacuum and gave purple oil. This oil was triturated with 200 ml of ether with constant manual stirring. During this time the oil became very thick. The ether solution was decanted and the oil was triturated with 100 ml of ether. The ether solution was decanted and the oil was again triturated with a 100 ml portion of ether. The ether was decanted and the combined ether solution was allowed to stand for about two hours to allow the triphenylphosphine oxide to crystallize. The ether solution was decanted from the crystals and the solid was washed with 100 ml of ether. The volume of the combined ether abstracts was reduced with vacuum until a volume of about 25 ml was obtained. This was allowed to stand over night at 0° C. Ether (10 ml) was added to the cold mixture, which was mixed to suspend the solid. The mixture was percolated through a column of 45 g of silica gel and eluted with ether; 75 ml fractions were collected. The fractions that contained product, as determined by thin layer chromatography, were pooled and the ether was removed with vacuum. This yielded 10.1 g of crude product. The material was flash chromatographed on silica gel with hexane, changing to 9:1 hexane:ether. The product-containing fractions were pooled and the solvents removed with vacuum. This yielded 7.4 g (57% yield) of pure product.

A mixture of 10% palladium on carbon (1 g) and a solution of the benzyl ester (10 g) in 150 ml of methanol was hydrogenolyzed at 25 psi for two hours. The mixture was filtered over celite and the residue was washed with methanol. The solvent was evaporated to give viscous oil in quantitative yield.

Reaction of the bromide with 1,1,2-trimethyl-[1H]-benz[e]indole was carried out as described in Example 1.

EXAMPLE 6

Bis(ethylcarboxymethyldihydroxyl)indocyanine Dye (FIG. 3)

The hydroxy-indole compound is readily prepared by a known method (P. L. Southwick, et al., One pot Fischer synthesis of (2,3,3-trimethyl-3-H-indol-5-yl)-acetic acid derivatives as intermediates for fluorescent biolabels. *Org. Prep. Proced. Int. Briefs,* 1988, 20(3), 279-284). Reaction of p-carboxymethylphenylhydrazine hydrochloride (30 mmol, 1 equiv.) and 1,1-bis(hydroxymethyl)propanone (45 mmole, 1.5 equiv.) in acetic acid (50 mL) at room temperature for 30 minutes and at reflux for one minute gives (3,3-dihydroxymethyl-2-methyl-3-H-indol-5-yl)-acetic acid as a solid residue. The reaction of 3-bromopropyl-N,N-bis(carboxymethyl) amine, which was prepared as described in Example 5, with the intermediate indole and subsequent reaction of the indole intermediate with glutaconaldehyde dianil monohydrochloride (see Example 1) gives the desired product.

EXAMPLE 7

Synthesis of Bis(propylcarboxymethyl)indocyanine Dye (FIG. 4)

The intermediate 2-chloro-1-formyl-3-hydroxymethylenecyclohexane was prepared as described in the literature (G. A. Reynolds and K. H. Drexhage, Stable heptamethine pyrylium dyes that absorb in the infrared. *J. Org. Chem.,* 1977, 42(5), 885-888). Equal volumes (40 mL each) of dimethylformamide (DMF) and dichloromethane were mixed and the solution was cooled to –10° C. in acetone-dry ice bath. Under argon atmosphere, phosphorus oxychloride (40 mL) in dichloromethane was added dropwise to the cool DMF solution, followed by the addition of 10 g of cyclohexanone. The resulting solution was allowed to warm up to room temperature and refluxed for six hours. After cooling to room temperature, the mixture was poured into ice-cold water and stored at 4° C. for twelve hours. About 8 g of yellow powder was obtained after filtration. Condensation of the cyclic dialdehyde with the indole intermediate is carried out as described in Example 1. Further functionalization of the dye with bis isopropylidene acetal protected monosaccharide was accomplished by the method described in the literature (J. H. Flanagan, et al., Near infrared heavy-atom-modified fluorescent dyes for base-calling in DNA-sequencing application using temporal discrimination. *Anal. Chem.,* 1998, 70(13), 2676-2684).

EXAMPLE 8

Synthesis of Bis(ethylcarboxymethyl)indocyanine Dye (FIG. 5)

These dyes are prepared as described in Example 7. These dyes absorb in the infrared region. The typical example shown in FIG. 5 has an estimated absorption maximum at 1036 nm.

EXAMPLE 9

Synthesis of Peptides

The procedure described below is for the synthesis of Octreotate. The amino acid sequence of Octreotate is: D-Phe-Cys'-Tyr-D-Trp-Lys-Thr-Cys'-Thr (SEQ ID NO:1), wherein Cys' indicates the presence of an intramolecular disulfide bond between two cysteine amino acids. Other peptides of this invention were prepared by a similar procedure with slight modifications in some cases.

The octapeptide was prepared by an automated fluorenylmethoxycarbonyl (Fmoc) solid phase peptide synthesis using a commercial peptide synthesizer from Applied Biosystems (Model 432A SYNERGY Peptide Synthesizer). The first peptide cartridge contained Wang resin pre-loaded with Fmoc-Thr on 25-μmole scale. Subsequent cartridges contained Fmoc-protected amino acids with side chain protecting groups for the following amino acids: Cys(Acm), Thr(t-Bu), Lys(Boc), Trp(Boc) and Tyr(t-Bu). The amino acid cartridges were placed on the peptide synthesizer and the product was synthesized from the C- to the N-terminal position. The coupling reaction was carried out with 75 μmoles of the protected amino acids in the presence of 2-(1H-benzotriazol-1-yl)-1,1,3,3-tetramethyluronium hexafluorophosphate (HBTU)/N-hydroxybenzotriazole (HOBt). The Fmoc protecting group was removed with 20% piperidine in dimethylformamide. After the synthesis was complete, the thiol group was cyclized with thallium trifluoroacetate and the product was cleaved from the solid support with a cleavage mixture containing trifluoroacetic acid (85%):water (5%):phenol (5%):thioanisole (5%) for 6 hours. The peptide was precipitated with t-butyl methyl ether and lyophilized with water:acetonitrile (2:3) mixture. The peptide was purified by HPLC and analyzed with LC/MS.

Octreotide, D-Phe-Cys'-Tyr-D-Trp-Lys-Thr-Cys'-Thr-OH (SEQ ID NO:2), wherein Cys' indicates the presence of an intramolecular disulfide bond between two cysteine amino acids, was prepared by the same procedure.

Bombesin analogs were prepared by the same procedure except that cyclization with thallium trifluoroacetate was not needed. Side-chain deprotection and cleavage from the resin was carried out with 50 μL each of ethanedithiol, thioanisole and water, and 850 μL of trifluoroacetic acid. Two analogues were prepared: Gly-Ser-Gly-Gln-Trp-Ala-Val-Gly-His-Leu-Met-NH$_2$ (SEQ ID NO:3) and Gly-Asp-Gly-Gln-Trp-Ala-Val-Gly-His-Leu-Met-NH$_2$ (SEQ ID NO:4).

Cholecystokinin octapeptide analogs were prepared as described for Octreotate without the cyclization step. Three analogs were prepared: Asp-Tyr-Met-Gly-Trp-Met-Asp-Phe-NH$_2$ (SEQ ID NO:5); Asp-Tyr-Nle-Gly-Trp-Nle-Asp-Phe-NH$_2$ (SEQ ID NO:6); and D-Asp-Tyr-Nle-Gly-Trp-Nle-Asp-Phe-NH$_2$ (SEQ ID NO:7) wherein Nle is norleucine.

A neurotensin analog, D-Lys-Pro-Arg-Arg-Pro-Tyr-Ile-Leu (SEQ ID NO:8), was prepared as described for Octreotate without the cyclization step.

EXAMPLE 10

Synthesis of Peptide-Dye Conjuqates (FIG. 6)

The method described below is for the synthesis of Octreotate-cyanine dye conjugates, but a similar procedure is used for the synthesis of other peptide-dye conjugates.

Octreotate was prepared as described in Example 9 but the peptide was not cleaved from the solid support and the N-terminal Fmoc group of Phe was retained. The thiol group was cyclized with thallium trifluoroacetate and the Phe was deprotected to liberate the free amine. Bisethylcarboxymethylindocyanine dye (53 mg, 75 μmoles) was added to an activation reagent consisting of a 0.2 M solution of HBTU/HOBt in DMSO (375 μL), and 0.2 M solution of diisopropylethylamine in DMSO (375 μL). The activation was complete in about 30 minutes and the resin-bound peptide (25 μmoles) was added to the dye. The coupling reaction was carried out at room temperature for three hours. The mixture was filtered and the solid residue was washed with DMF, acetonitrile and THF. After drying the green residue, the peptide was cleaved from the resin and the side chain protecting groups were removed with a mixture of 85% trifluoroacetic acid, 2.5% water, 2.5% thioanisole and 2.5% phenol. The resin was filtered and cold t-butyl methyl ether (MTBE) was used to precipitate the dye-peptide conjugate, which was dissolved in acetonitrile:water (2:3) mixture and lyophilized. The product was purified by HPLC to give the monoOctreotate-Bismethylcarboxymethylindocyanine dye (Cytate 1, 80%) and the bisOctreotate-Bismethylcarboxymethylindocyanine dye (Cytate 2, 20%). The monoOctreotate conjugate is obtained almost exclusively (>95%) over the bis conjugate by reducing the reaction time to two hours. However, this also leads to incomplete reaction, and the free Octreotate must be carefully separated from the dye conjugate in order to avoid saturation of the receptors by the non-dye conjugated peptide.

Octreotate-bispentylcarboxymethylindocyanine dye was prepared as described above with some modifications. Bispentylcarboxymethylindocyanine dye (60 mg, 75 μmoles) was added to an activation reagent consisting of a 0.2 M solution of HBTU/HOBt in DMSO (400 μL), and 0.2 M solution of diisopropylethylamine in DMSO (400 μL). The activation was complete in about 30 minutes and the resin-bound peptide (25 μmoles) was added to the dye. The reaction was carried out at room temperature for three hours. The mixture was filtered and the solid residue was washed with DMF, acetonitrile and THF. After drying the green residue, the peptide was cleaved from the resin and the side chain protecting groups were removed with a mixture of 85% trifluoroacetic acid, 2.5% water, 2.5% thioanisole and 2.5% phenol. The resin was filtered and cold t-butyl methyl ether (MTBE) was used to precipitate the dye-peptide conjugate, which was dissolved in an acetonitrile:water (2:3) mixture and lyophilized. The product was purified by HPLC to give Octreotate-1,1,2-trimethyl-[1H]-benz[e]indole propanoic acid conjugate (10%), monoOctreotate-bispentylcarboxymethylindocyanine dye (Cytate 3, 60%) and bisOctreotate-bispentylcarboxymethylindocyanine dye (Cytate 4, 30%).

EXAMPLE 11

Formulation of Peptide-Dye Conjugates in Dimethyl Sulfoxide (DMSO)

The dye-peptide conjugates are sparingly soluble in water and require the addition of solubilizing agents or co-solvents. Addition of 1-20% aqueous ethanol to the conjugates partially quenched the fluorescence intensity in vitro and the fluorescence was completely quenched in vivo (the conjugate was not detected by the charged coupled device (CCD) camera). Addition of 1-50% of DMSO either re-established or increased the fluorescence intensity of the conjugates in vitro and in vivo. The dye fluorescence remained intense for over one week. The DMSO formulations were well tolerated by experimental animals used for this invention.

EXAMPLE 12

Imaging of Pancreatic Ductal Adenocarcinoma (DSL 6A) with Indocyanine Green (ICG)

A non-invasive in vivo fluorescence imaging apparatus was employed to assess the efficacy of contrast agents developed for tumor detection in animal models. A LaserMax Inc. laser diode of nominal wavelength 780 nm and nominal power of 40 mW was used. The detector was a Princeton Instruments model RTE/CCD-1317-K/2 CCD camera with a Rodenstock 10 mm F2 lens (stock #542.032.002.20) attached. An 830 nm interference lens (CVI Laser Corp., part # F10-830-4-2) was mounted in front of the CCD input lens such that only emitted fluorescent light from the contrast agent was imaged. Typically, an image of the animal was taken pre-injection of contrast agent. This image was subsequently subtracted (pixel by pixel) from the post injection images. However, the background subtraction was never done once the animal had been removed from the sample area and returned at a later time for images taken several hours post injection.

DSL 6A tumors were induced in male Lewis rats in the left flank area by the introduction of material from a solid (donor) implant and the tumors were palpable in approximately 14 days. The animals were anesthetized with xylazine; ketamine; acepromazine 1.5: 1.5: 0.5 at 0.8 mL/kg via intramuscular injection. The area of the tumor (left flank) was shaved to expose tumor and surrounding surface area. A 21 gauge butterfly equipped with a stopcock and two syringes containing heparinized saline was placed into the later tail vein of the rat. Patency of the vein was checked prior to administration of the ICG via the butterfly apparatus. Each animal received 500 mL of a 0.42 mg/mL solution of ICG in water.

Figure 7E:
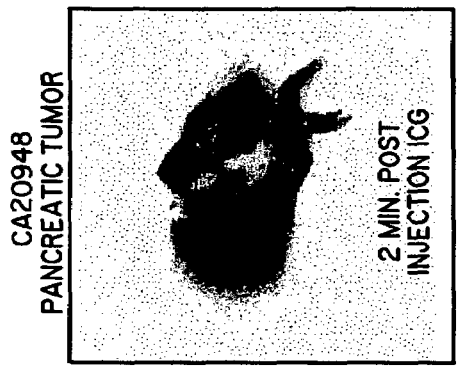
FIGS. 7A-F represent images at 2 minutes and 30 minutes post injection of indocyanine green (ICG) into rats with various tumors.
Figure 7F:
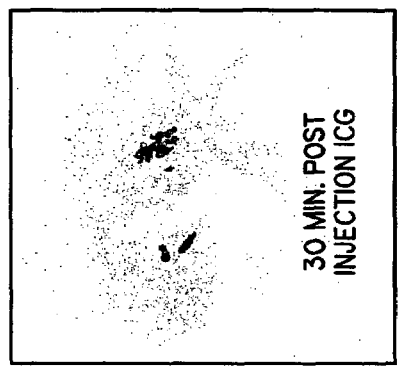
Figure 7C:
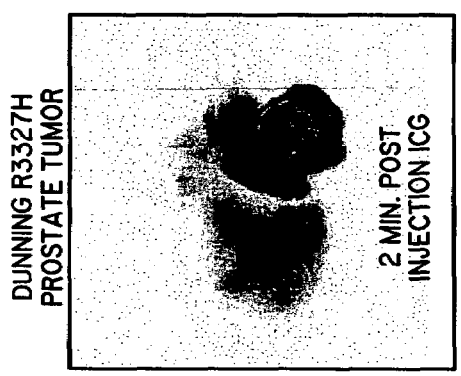
Figure 7D:
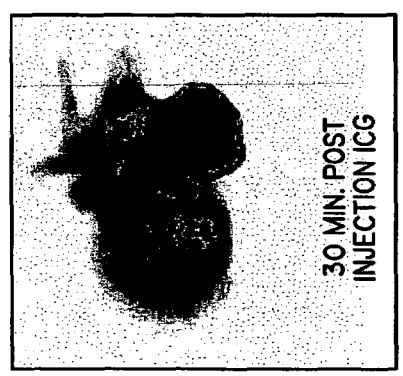
Figure 7A:
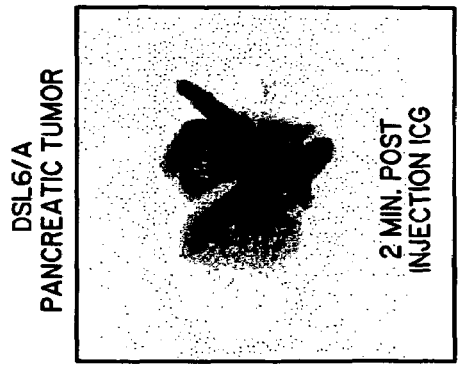
Figure 7B:
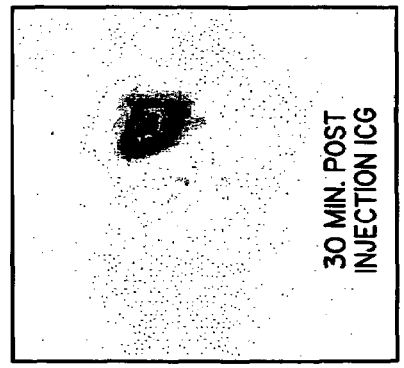

FIGS. 7A-B are tumor images of two minutes (FIG. 7A) and 30 minutes (FIG. 7B) post bolus injection of a 0.5 ml aqueous solution of ICG (5.4 µm). Tetracarboxylic acid cyanine dyes were synthesized as shown in FIG. 2, with $A=CH_2$ or $CH_2OCH_2$; $R_1=R_2=H$ (Formula 1) or $R_1$, $R_2$=fused phenyl (Formula 2).

The Figures are false color images of fluorescent intensity measured at the indicated times, with images constrained to the tumor and a small surrounding area. As is shown, the dye intensity in the tumor is considerably diminished 30 minutes post-ICG injection.

EXAMPLE 13

Imaging of Prostatic Carcinoma (R3327-H) with Indocyanine Green (ICG)

The imaging apparatus and the procedure used are described as in Example 12. Prostrate tumors (Dunning R3327-H) were induced in young male Copenhagen rats in the left flank area from a solid implant. These tumors grow very slowly and palpable masses were present 4-5 months post implant. FIGS. 7C-D are images of a rat with an induced prostatic carcinoma tumor (R3327-H) imaged at two minutes (FIG. 7C) and 30 minutes (FIG. 7D) post injection.

The Figures are false color images of fluorescent intensity measured at the indicated times, with images constrained to the tumor and a small surrounding area. As is shown, the dye intensity in the tumor is considerably diminished 30 minutes post-ICG injection.

EXAMPLE 14

Imaging of Rat Pancreatic Acinar Carcinoma (CA20948) with Indocyanine Green (ICG)

The imaging apparatus and the procedure used are described in Example 12. Rat pancreatic acinar carcinoma expressing the SST-2 receptor (CA20948) was induced by solid implant technique in the left flank area, and palpable masses were detected nine days post implant. The images obtained at 2 and 30 minutes post injection are shown in FIG. 7E-F.

FIGS. 7E-F are images of a rat with an induced pancreatic acinar carcinoma (CA20948) expressing the SST-2 receptor imaged at two minutes (FIG. 7E) and 30 minutes (FIG. 7F) post injection.

The Figures are false color images of fluorescent intensity measured at the indicated times, with images constrained to the tumor and a small surrounding area. As is shown, the dye intensity in the tumor is considerably diminished and almost absent 30 minutes post-ICG injection.

EXAMPLE 15

Imaging of Rat Pancreatic Acinar Carcinoma (CA20948) with Cytate 1

The imaging apparatus and the procedure used are described in Example 12 except that each animal received 500 µl of a 1.0 mg/mL solution of Cytate 1 solution of 25% dimethylsulfoxide in water.

Rat pancreatic acinar carcinoma expressing the SST-2 receptor (CA20948) were induced by solid implant technique in the left flank area, and palpable masses were detected 24 days post implant. Images were obtained at various times post injection. Uptake into the tumor was seen at two minutes but was not maximal until about five minutes.

Figure 8A:
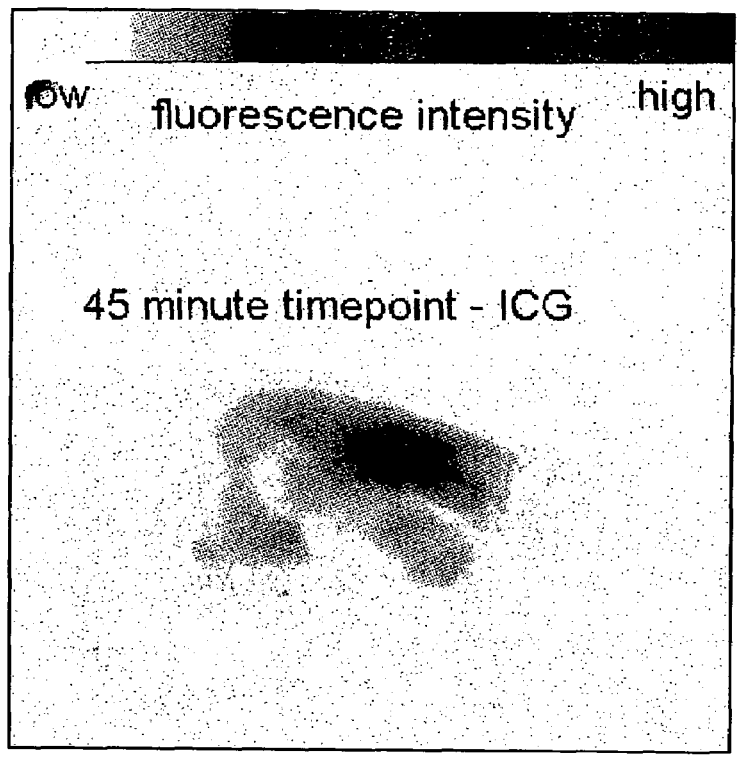
FIGS. 8A-B show a comparison of the uptake of ICG (FIG. 8A) and Cytate 1 (FIG. 8B) in rats with the pancreatic acinar carcinoma (CA20948).
Figure 8B:
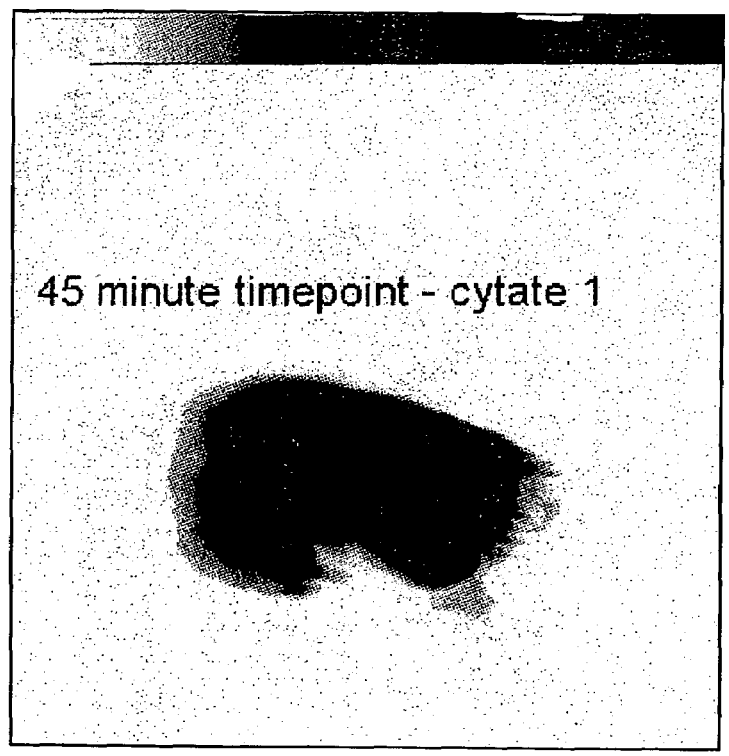

FIGS. 8A-B show a comparison of the uptake of ICG and Cytate 1 at 45 minutes in rats with the CA20948 tumor cell line. By 45 minutes the ICG has mostly cleared (FIG. 8A) whereas the Cytate 1 is still quite intense (FIG. 8B). This dye fluorescence remained intense in the tumor for several hours post-injection.

EXAMPLE 16

Imaging of Rat Pancreatic Acinar Carcinoma(CA20948) with Cytate 1 Compared with Imaging with Indocyanine Green Using indocyanine green (ICG), three different tumor lines were imaged optically using a CCD camera apparatus. Two of the lines, DSL 6/A (pancreatic) and Dunning R3327H (prostate) indicated slow perfusion of the agent over time into the tumor and reasonable images were obtained for each. The third line, CA20948 (pancreatic), indicated only a slight but transient perfusion that was absent after only 30 minutes post injection. This indicated no non-specific localization of ICG into this line compared to the other two tumor lines, suggesting a different vascular architecture for this type of tumor (see FIGS. 7A-F). The first two tumor lines (DSL 6/A and R3327H) are not as highly vascularized as CA20948 which is also rich in somatostatin (SST-2) receptors. Consequently, the detection and retention of a dye in this tumor model is a good index of receptor-mediated specificity.

Figure 9A:
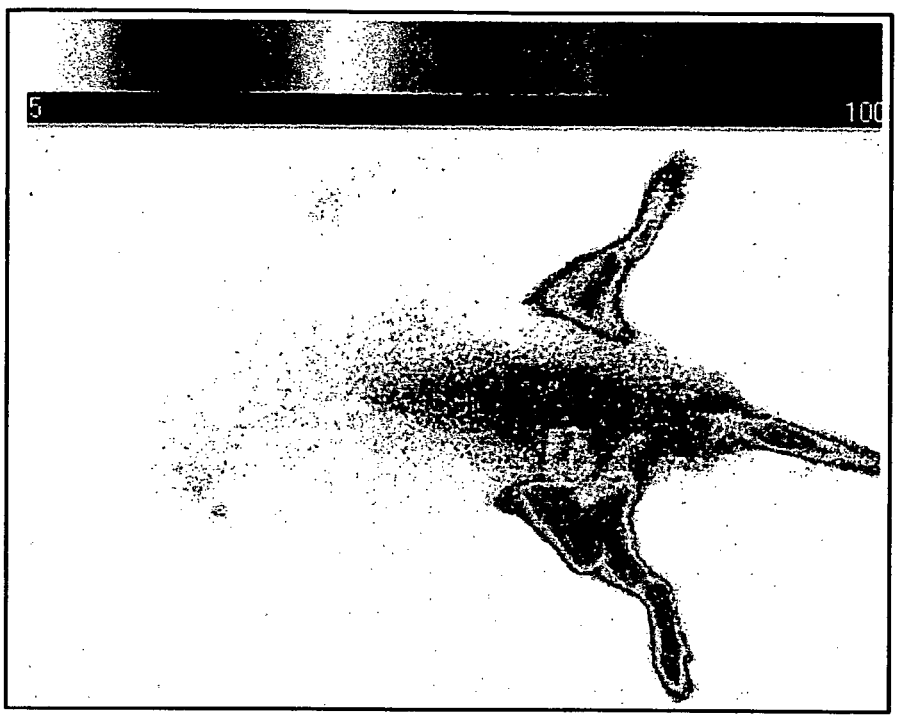
FIGS. 9A-B show images of rats with the pancreatic acinar carcinoma (CA20948) 45 minutes (FIG. 9A) and 27 hours (FIG. 9B) post injection of Cytate 1.
Figure 9B:
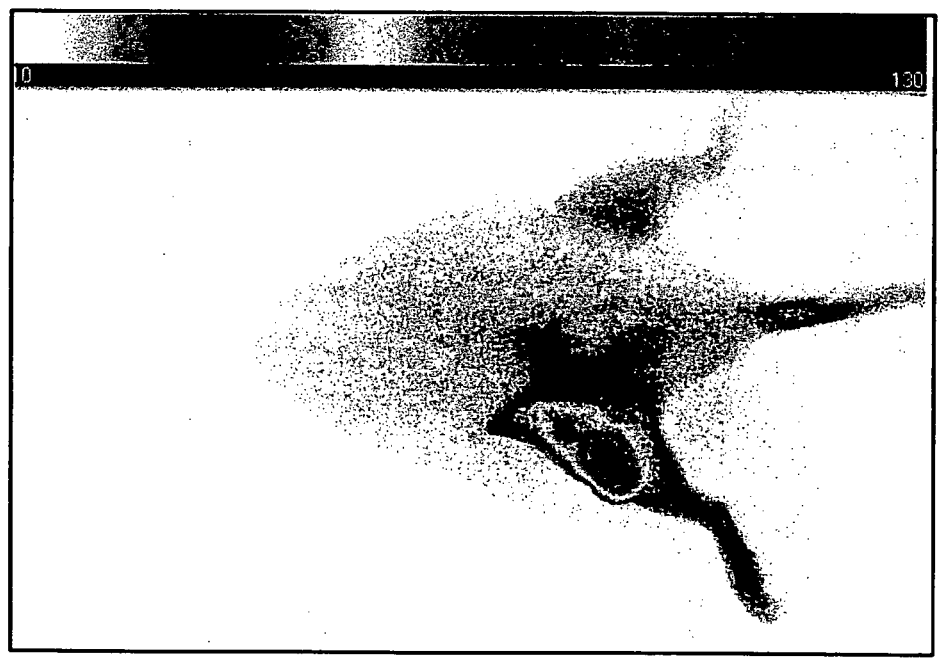

Octreotate is known to target somatostatin (SST-2) receptors, hence, cyano-Octreotates (Cytate 1 and Cytate 2) was prepared. Cytate 1 was evaluated in the CA20948 Lewis rat model. Using the CCD camera apparatus, localization of this dye was observed in the tumor (indicated by arrow) at 45 minutes post injection (FIG. 9A). At 27 hours post injection, the animal was again imaged (FIG. 9B). Tumor visualization was easily observed (indicated by arrow) showing specificity of this agent for the SST-2 receptors present in the CA20948 tumor line.

Figure 10:
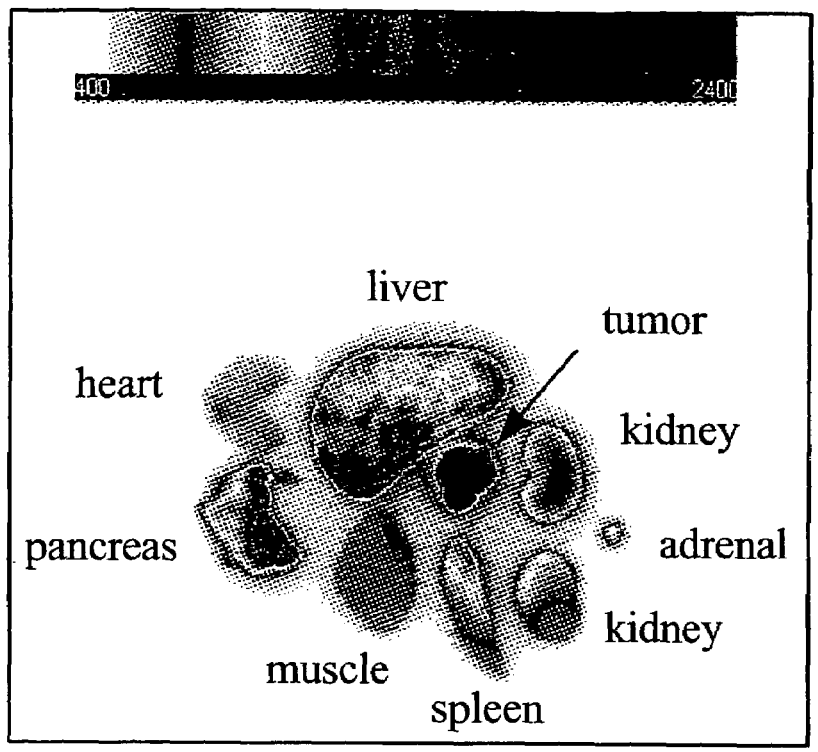
FIG. 10 is an image of individual organs taken from a rat with pancreatic acinar carcinoma (CA20948) about 24 hours after injection with Cytate 1.

Individual organs were removed at about 24 hours post Cytate 1 administration and imaged. As shown in FIG. 10, high uptake of Cytate 1 was observed in the pancreas, adrenals and tumor tissue, while heart, muscle, spleen and liver indicated significantly lower uptake. These data correlate well with radiolabeled Octreotate in the same model system (M. de Jong, et al. *Cancer Res.* 1998, 58, 437-441).

EXAMPLE 17

Imaging of Rat Pancreatic Acinar Carcinoma (AR42-J) with Bombesinate

The AR42-J cell line is derived from exocrine rat pancreatic acinar carcinoma. It can be grown in continuous culture or maintained in vivo in athymic nude mice, SCID mice, or in Lewis rats. This cell line is particularly attractive for in vitro receptor assays, as it is known to express a variety of hormone receptors including cholecystokinin (CCK), epidermal growth factor (EGF), pituitary adenylate cyclase activating peptide (PACAP), somatostatin (SST-2) and bombesin.

In this model, male Lewis rats were implanted with solid tumor material in a similar manner as described for the CA20948 rat model. Palpable masses were present seven days post implant, and imaging studies were conducted on animals at 10-12 days post implant when the mass had achieved about 2-2.5 g.

Figure 11:
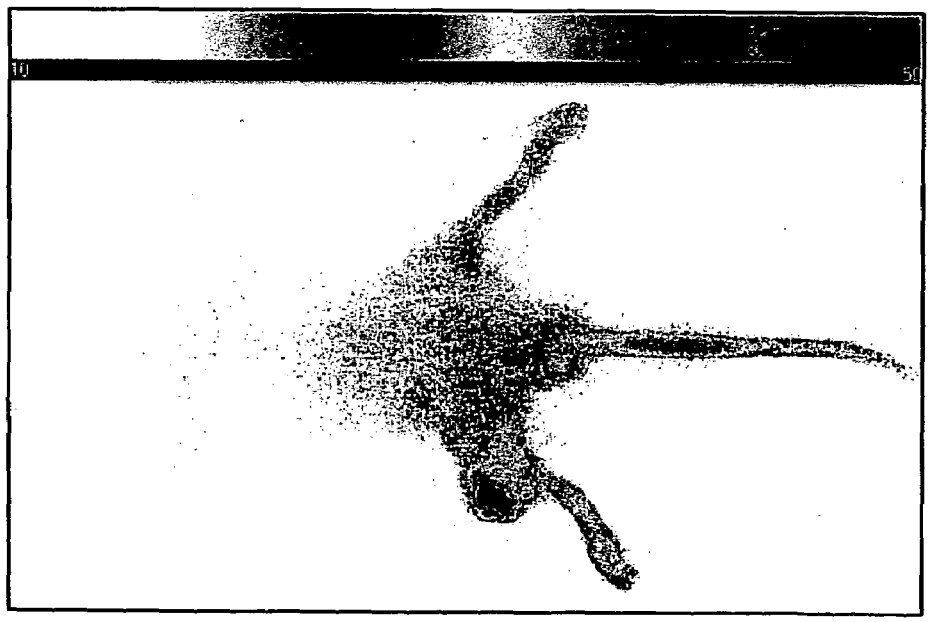
FIG. 11 is an image of bombesinate in an AR42-J tumor-bearing rat 22 hours after injection.

FIG. 11 is an image of bombesinate in an AR42-J tumor-bearing rat, as described in Example 16, at 22 hours post injection of bombesinate. As shown in FIG. 11, specific localization of the bioconjugate in the tumor (indicated by arrow) was observed.

EXAMPLE 18

Monitoring of the Blood Clearance Profile of Peptide-Dye Conjugates

A laser of appropriate wavelength for excitation of the dye chromophore was directed into one end of a fiber optic bundle and the other end was positioned a few millimeters from the ear of a rat. A second fiber optic bundle was also positioned near the same ear to detect the emitted fluorescent light and the other end was directed into the optics and electronics for data collection. An interference filter (IF) in the collection optics train was used to select emitted fluorescent light of the appropriate wavelength for the dye chromophore.

Sprague-Dawley or Fischer 344 rats were used in these studies. The animals were anesthetized with urethane administered via intraperitoneal injection at a dose of 1.35 g/kg body weight. After the animals had achieved the desired plane of anesthesia, a 21 gauge butterfly with 12" tubing was placed in the lateral tail vein of each animal and flushed with heparinized saline. The animals were placed onto a heating pad and kept warm throughout the entire study. The lobe of the left ear was affixed to a glass microscope slide to reduce movement and vibration.

Incident laser light delivered from the fiber optic was centered on the affixed ear. Data acquisition was then initiated, and a background reading of fluorescence was obtained prior to administration of the test agent. For Cytates 1 or 2, the peptide-dye conjugate was administered to the animal through a bolus injection, typically 0.5 to 2.0 ml, in the lateral tail vein. This procedure was repeated with several dye-peptide conjugates in normal and tumor bearing rats. Representative profiles as a method to monitor blood clearance of the peptide-dye conjugate in normal and tumor bearing animals are shown in FIGS. 12-16. The data were analyzed using a standard sigma plot software program for a one compartment model.

Figure 12:
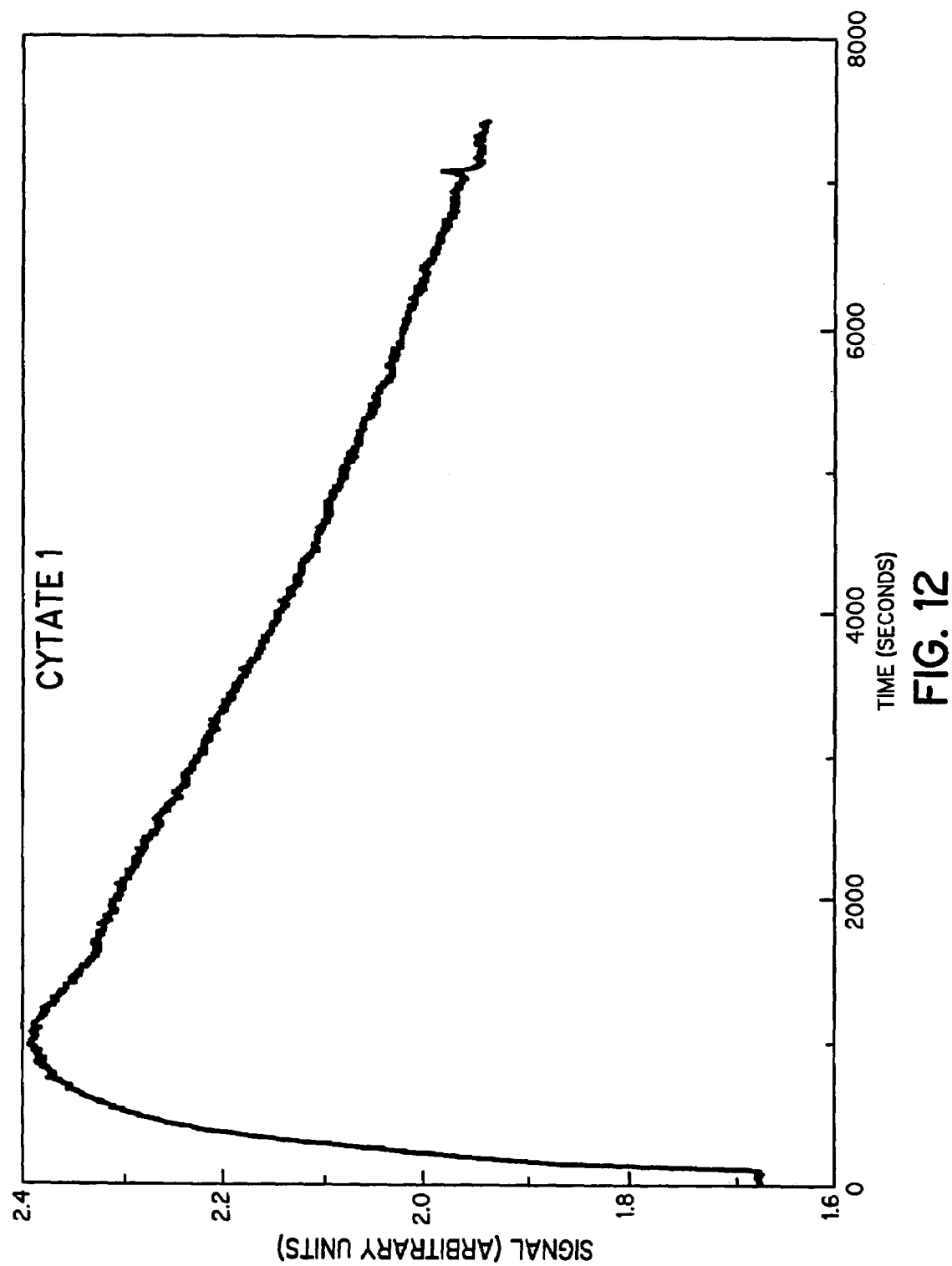
FIG. 12 is the clearance profile of Cytate 1 from the blood of a normal rat.
Figure 13:
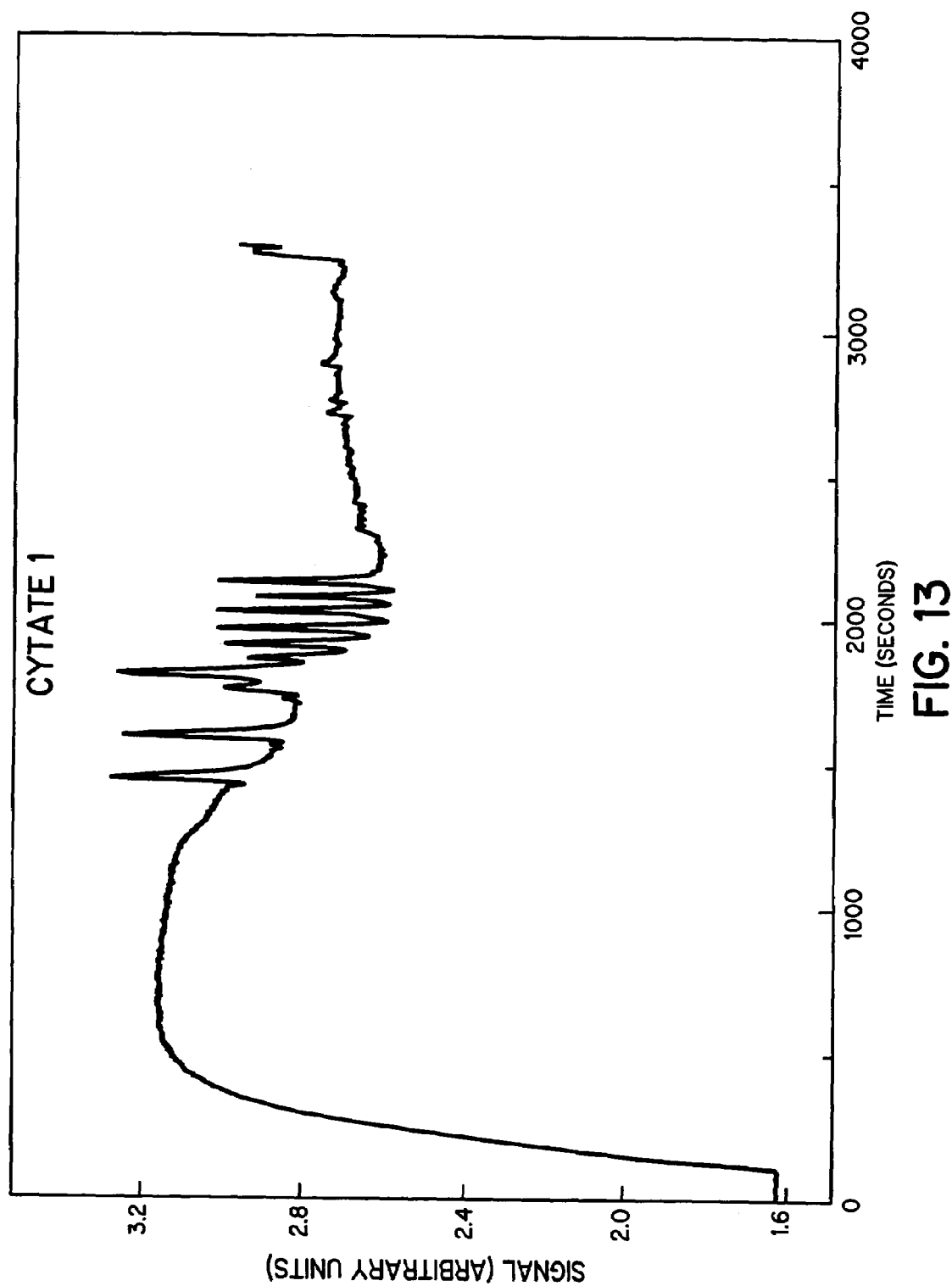
FIG. 13 is the clearance profile of Cytate 1 from the blood of a pancreatic tumor-bearing rat.

In rats treated with Cytates 1 or 2, the fluorescence signal rapidly increased to a peak value. The signal then decayed as a function of time as the conjugate cleared from the blood stream. FIG. 12 shows the clearance profile of Cytate 1 from the blood of a normal rat monitored at 830 nm after excitation at 780 nm. FIG. 13 shows the clearance profile of Cytate 1 from the blood of a pancreatic tumor (CA20948)-bearing rat also monitored an 830 nm after excitation at 780 nm.

Figure 14:
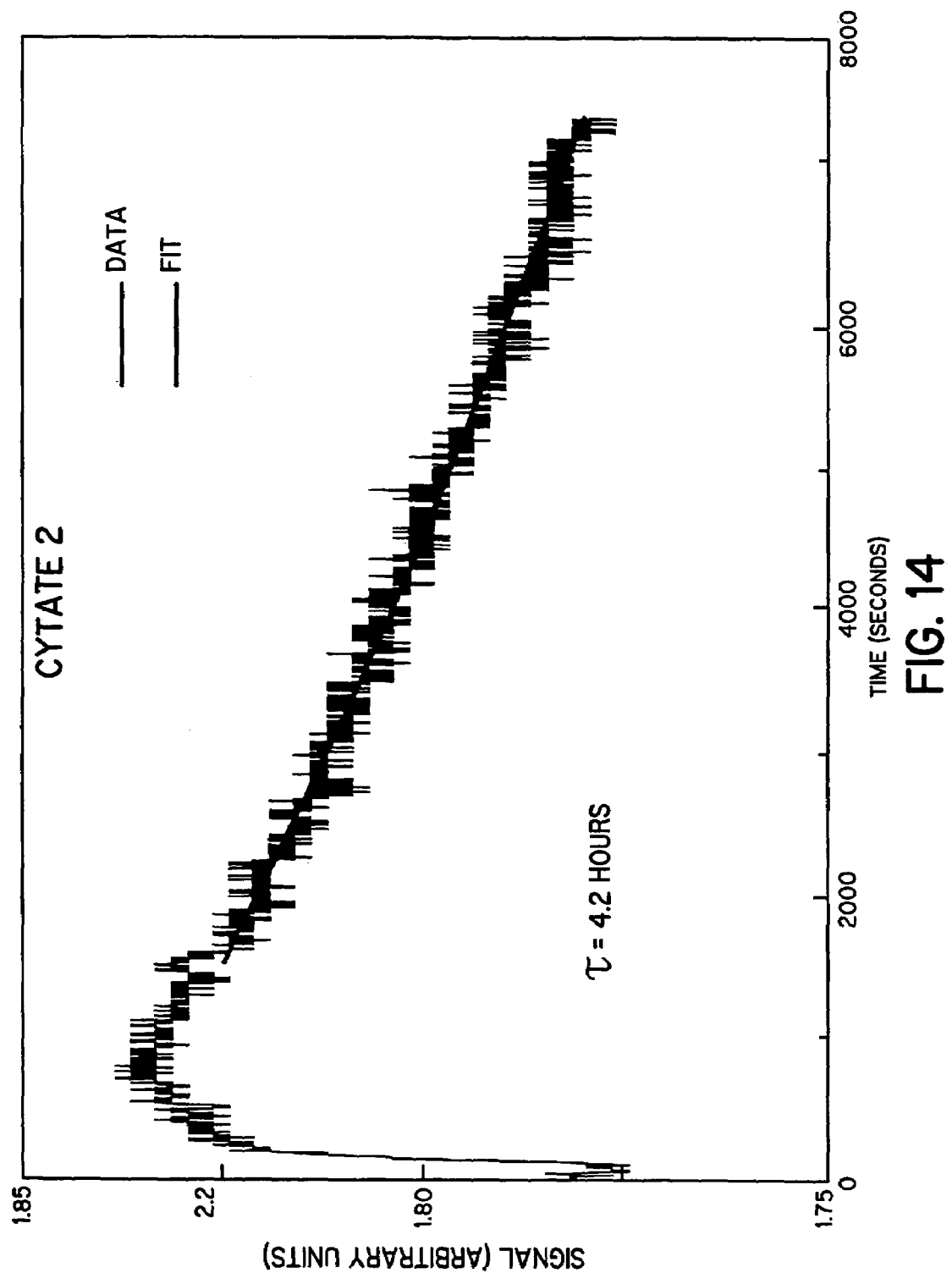
FIG. 14 is the clearance profile of Cytate 2 from the blood of a normal rat.
Figure 15:
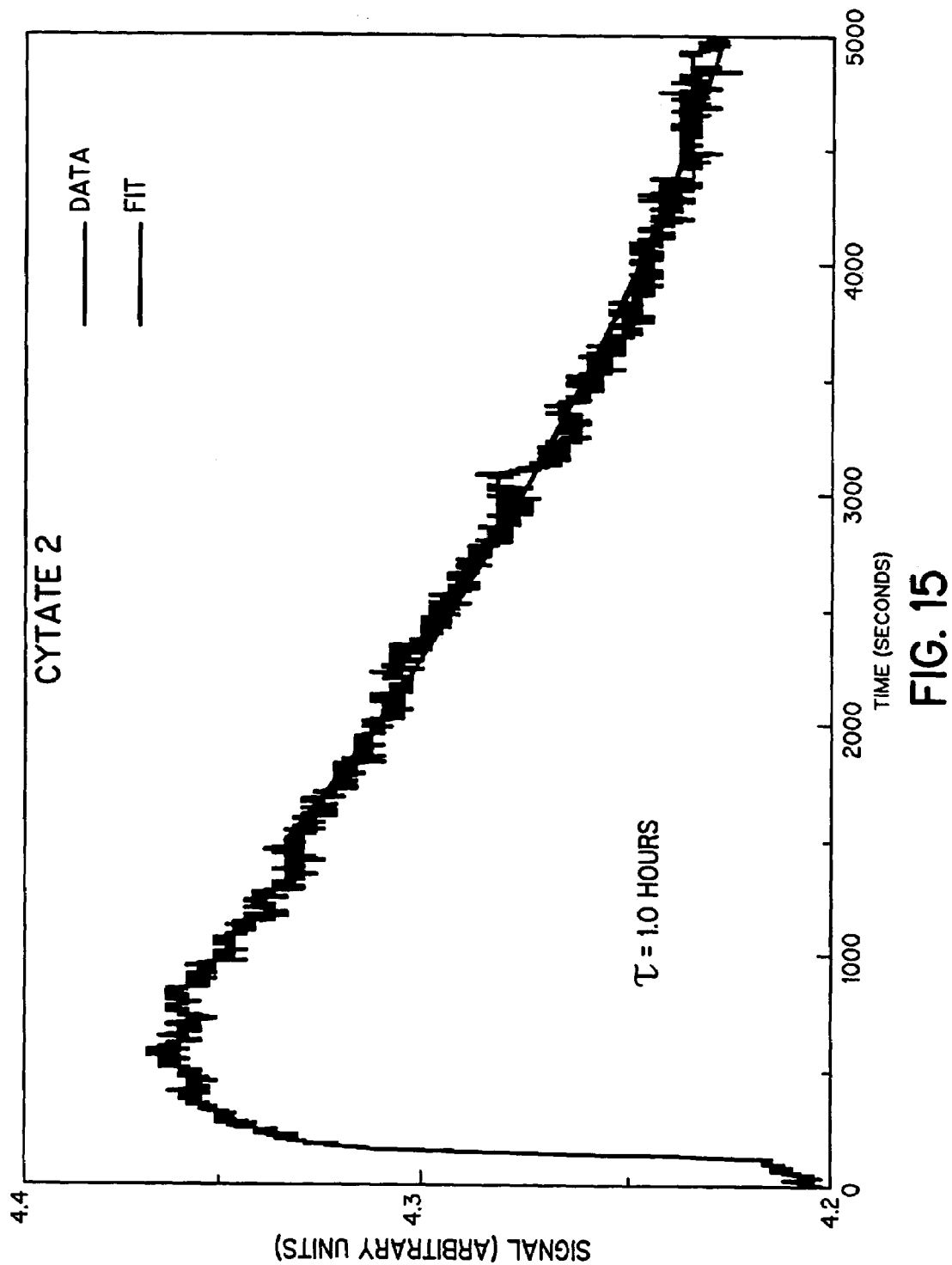
FIG. 15 is the clearance profile of Cytate 2 from the blood of a pancreatic tumor-bearing rat.

FIG. 14 shows the clearance profile of Cytate 2 from the blood of a normal rat, and FIG. 15 shows the clearance profile of Cytate 2 from the blood of a pancreatic tumor (CA20948)-bearing rat, monitored at 830 nm after excitation at 780 nm.

Figure 16:
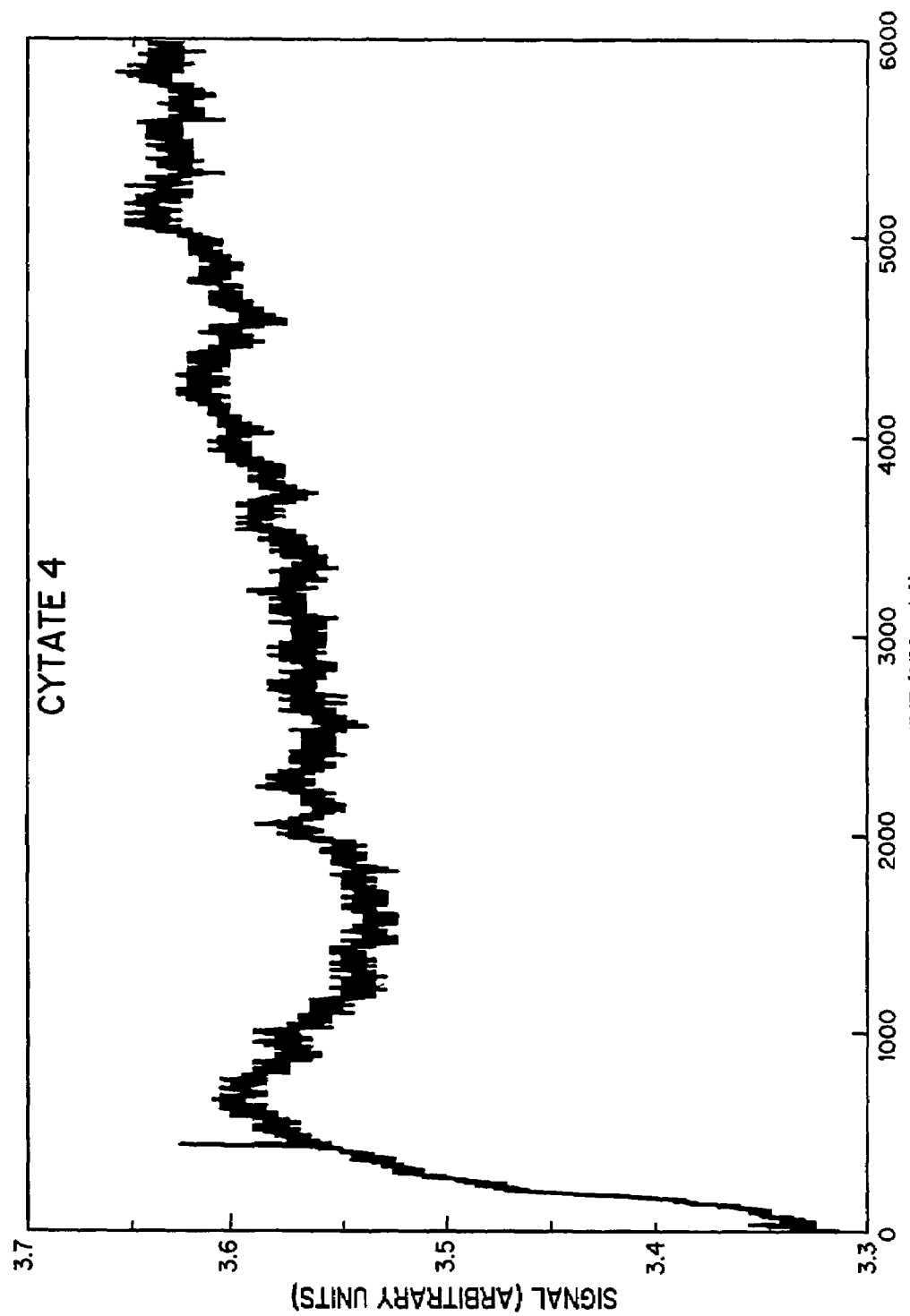
FIG. 16 is the clearance profile of Cytate 4 from the blood of a normal rat.

FIG. 16 shows the clearance profile of Cytate 4 from the blood of a normal rat, monitored at 830 nm after excitation at 780 nm.

It should be understood that the embodiments of the present invention shown and described in the specification are only specific embodiments of inventors who are skilled in the art and are not limiting in any way. Therefore, various changes, modifications, or alterations to those embodiments may be made or resorted to without departing from the spirit of the invention in the scope of the following claims. The references cited are expressly incorporated by reference herein in their entirety.

What is claimed is:

1. A compound of the following formula, wherein:

each A is independently —$CH_2$ or —$CH_2OCH_2$;
R is —CONH-peptide;
R' is R or —COOH; and
each n is independently 1-6.

2. The compound of claim 1, wherein R' is R.
3. The compound of claim 1, wherein R' is —COOH.
4. The compound of claim 1, wherein peptide is octreotide.
5. The compound of claim 1, wherein peptide is octreotate.
6. The compound of claim 1, wherein peptide is bombesin.
7. The compound of claim 1, wherein peptide is cholecystokinin.
8. The compound of claim 1, wherein peptide is neurotensin.
9. The compound of claim 1, wherein n is 1.
10. The compound of claim 1, wherein n is 4.
11. The compound of claim 1, wherein n is 6.
12. The compound of claim 1, wherein each A is —$CH_2$, and each n is 1.
13. The compound of claim 12, wherein R' is —COOH.
14. The compound of claim 13, wherein peptide is octreotate.
15. The compound of claim 13, wherein peptide is octreotide.
16. The compound of claim 13, wherein peptide is octreotate.
17. The compound of claim 13, wherein peptide is bombesin.
18. The compound of claim 13, wherein peptide is cholecystokinin.
19. The compound of claim 13, wherein peptide is neurotensin.
20. The compound of claim 12, wherein R' is R, and peptide is octreotate.

* * * * *